US007479122B2

(12) United States Patent
Ceriani et al.

(10) Patent No.: US 7,479,122 B2
(45) Date of Patent: Jan. 20, 2009

(54) FRAME FOR AN ORTHOPEDIC BRACE INCLUDING OFFSET HINGES

(75) Inventors: Dylann D. Ceriani, San Diego, CA (US); Bradley R. Mason, Rancho Santa Fe, CA (US)

(73) Assignee: Breg, Inc., Vista, CA (US)

( * ) Notice: Subject to any disclaimer, the term of this patent is extended or adjusted under 35 U.S.C. 154(b) by 779 days.

(21) Appl. No.: 11/040,814

(22) Filed: Jan. 22, 2005

(65) Prior Publication Data

US 2006/0167394 A1 Jul. 27, 2006

(51) Int. Cl.
*A61F 5/00* (2006.01)
(52) U.S. Cl. .......................................... 602/16; 602/26
(58) Field of Classification Search .................. 602/5, 602/16, 20–23, 26–27; 128/882
See application file for complete search history.

(56) References Cited

U.S. PATENT DOCUMENTS

| 1,510,408 | A | | 9/1924 | Lychou | |
|---|---|---|---|---|---|
| 3,703,171 | A | | 11/1972 | Schlavitto | 128/80 C |
| 3,799,159 | A | | 3/1974 | Scott | 128/80 C |
| 3,928,872 | A | | 12/1975 | Johnson | 2/22 |
| 4,130,115 | A | | 12/1978 | Taylor | 128/80 C |
| 4,219,892 | A | | 9/1980 | Rigdon | 2/24 |
| 4,372,298 | A | | 2/1983 | Lerman | 128/80 C |
| 4,628,916 | A | * | 12/1986 | Lerman et al. | 602/16 |
| 4,805,606 | A | * | 2/1989 | McDavid, III | 602/26 |
| 4,928,676 | A | | 5/1990 | Pansiera | 128/80 F |
| 4,940,044 | A | | 7/1990 | Castillo | 128/80 C |
| 5,002,045 | A | | 3/1991 | Spademan | |
| 5,022,391 | A | * | 6/1991 | Weidenburner | 602/16 |
| 5,302,169 | A | | 4/1994 | Taylor | 602/16 |
| 5,336,160 | A | | 8/1994 | Christensen | 602/6 |
| 5,400,806 | A | | 3/1995 | Taylor | 128/898 |
| 5,431,623 | A | | 7/1995 | Rice | 602/26 |
| 5,669,873 | A | | 9/1997 | Towsley | 602/26 |
| 5,730,710 | A | | 3/1998 | Eichhorn et al. | 602/26 |
| 5,766,140 | A | | 6/1998 | Tillinghast, III et al. | 602/16 |
| 5,823,981 | A | | 10/1998 | Grim et al. | 602/26 |
| 6,110,137 | A | | 8/2000 | Bastyr et al. | 602/26 |
| 6,527,733 | B1 | | 3/2003 | Ceriani et al. | 602/16 |
| 6,540,709 | B1 | | 4/2003 | Smits | 602/16 |
| 6,572,571 | B2 | | 6/2003 | Lowe | 602/5 |
| 2003/0149386 | A1 | | 8/2003 | Ceriani et al. | 602/26 |
| 2004/0097859 | A1 | | 5/2004 | Stearns | 602/26 |

FOREIGN PATENT DOCUMENTS

| EP | 1302184 A1 | 4/2003 |
|---|---|---|
| FR | 2862205 A1 | 5/2005 |
| WO | WO 03/065943 A1 | 8/2003 |

* cited by examiner

*Primary Examiner*—Michael A. Brown
(74) *Attorney, Agent, or Firm*—Rodney F. Brown

(57) ABSTRACT

A frame is provided for an orthopedic brace having a frame assembly and an opposing frame assembly. The frame assembly includes a first longitudinal support and a second longitudinal support rotatably connected by a rotational hinge. The opposing frame assembly includes a first opposing longitudinal support and a second opposing longitudinal support rotatably connected by an opposing rotational hinge. The first longitudinal support has a greater degree of flexibility than the first opposing longitudinal support and/or the second longitudinal support has a greater degree of flexibility than the second opposing longitudinal support to enhance the fit of the frame with the body of a user.

27 Claims, 9 Drawing Sheets

FRAME FOR AN ORTHOPEDIC BRACE INCLUDING OFFSET HINGES

TECHNICAL FIELD

The present invention relates generally to orthopedic braces, and more particularly to an orthopedic brace having a frame, which includes one or more offset hinges.

BACKGROUND OF THE INVENTION

Orthopedic braces embody a broad range of structures, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury while the joint is rehabilitated.

Conventional orthopedic braces typically include a frame consisting of a plurality of rigid support members positioned adjacent to the body on either side of the skeletal joint being stabilized. The rigid support members are dynamically interconnected by one or more rotational hinges, which are positioned adjacent to the skeletal joint being stabilized. Thus, a conventional knee brace typically includes a frame having a rigid upper support member positioned adjacent to the upper leg and a rigid lower support member positioned adjacent to the lower leg. A rotational hinge positioned adjacent to the knee dynamically interconnects the rigid upper and lower support members. The knee brace is typically secured to the leg by a plurality of straps.

A precise fit of the knee brace with the leg is often critical to the proper function of the knee brace and to the comfort of the user. However, even if a knee brace achieves a precise fit to the leg at the outset, the size of the leg can change over time due to a number of factors, such as swelling, muscle atrophy, or muscle build-up, which diminishes the precision of the fit. The present invention recognizes the need for orthopedic braces which provide a precise fit with the body of a user and which correspondingly exhibit acceptable functional performance characteristics. Accordingly, it is an object of the present invention to provide an orthopedic brace which provides a precise fit with the body of the user to which the orthopedic brace is secured. In particular, it is an object of the present invention to provide a precise-fitting orthopedic brace which is adaptable to variations in the dimensions of the body of the user over time. It is further an object of the present invention to provide such a precise-fitting orthopedic brace which exhibits acceptable functional performance characteristics in supporting and/or stabilizing a skeletal joint of the user. These objects and others are accomplished in accordance with the invention described hereafter.

SUMMARY OF THE INVENTION

The present invention is a frame for an orthopedic brace. The frame has a frame assembly and an opposing frame assembly. The frame assembly includes a first longitudinal support and a second longitudinal support rotatably connected by a rotational hinge. The opposing frame assembly includes a first opposing longitudinal support and a second opposing longitudinal support rotatably connected by an opposing rotational hinge. The first longitudinal support has a greater degree of flexibility than the first opposing longitudinal support and/or the second longitudinal support has a greater degree of flexibility than the second opposing longitudinal support.

Another characterization of the present invention is an orthopedic brace comprising a frame assembly, an opposing frame assembly, an upper frame assembly member and a lower frame assembly member. The frame assembly includes an upper longitudinal support and a lower longitudinal support rotatably connected by a rotational hinge which is essentially rigid in a mediolateral direction. The upper longitudinal support includes a first upper frame member, a second upper frame member, a first upper offset hinge, and a second upper offset hinge. The first upper offset hinge connects the first and second upper frame members and has a greater degree of flexibility than the first and second upper frame members in the mediolateral direction. The lower longitudinal support includes a first lower frame member, a second lower frame member, a first lower offset hinge, and a second lower offset hinge. The first lower offset hinge connects the first and second lower frame members and has a greater degree of flexibility than the first and second lower frame members in the mediolateral direction.

The opposing frame assembly includes an upper opposing longitudinal support and a lower opposing longitudinal support rotatably connected by an opposing rotational hinge. The upper longitudinal support has a greater degree of flexibility than the upper opposing longitudinal support and/or the lower longitudinal support has a greater degree of flexibility than the lower opposing longitudinal support. The frame assembly is a medial frame assembly and the opposing frame assembly is a lateral frame assembly. Alternatively, the frame assembly is a lateral frame assembly and the opposing frame assembly is a medial frame assembly.

The upper frame assembly member connects the upper longitudinal support and the upper opposing longitudinal support. The second upper offset hinge connects the second upper frame member and the upper frame assembly member and has a greater degree of flexibility than the second upper frame member and the upper frame assembly member in the mediolateral direction. The lower frame assembly member connects the lower longitudinal support and the lower opposing longitudinal support. The second lower offset hinge connects the second lower frame member and the lower frame assembly member and has a greater degree of flexibility than the second lower frame member and the lower frame assembly member in the mediolateral direction.

In accordance with numerous embodiments of the orthopedic brace, the first upper or lower frame member is a central connector engaging the rotational hinge and the second upper or lower frame member is a sidebar. The central connector is constructed from a metal, the sidebar is constructed from a metal or a plastic and the first upper or lower offset hinge is constructed from the plastic of the sidebar or a different plastic. The first upper or lower offset hinge is preferably attached to the central connector by overmolding. The upper or lower frame assembly member is a cuff constructed from a metal and the second upper or lower offset hinge is attached to the cuff by overmolding or by at least one fastener.

Another characterization of the present invention is a method for precisely fitting a knee brace with a leg of a user. A knee brace is provided having a frame assembly and an opposing frame assembly. The frame assembly includes an upper longitudinal support and a lower longitudinal support rotatably connected by a central joint. The upper and/or lower longitudinal support includes a first frame member and a second frame member connected by an offset hinge. The first and second frame members are less flexible than the offset hinge. The opposing frame assembly includes an opposing upper longitudinal support and an opposing lower longitudinal support rotatably connected by an opposing lateral central joint.

The knee brace is placed on a leg such that the upper longitudinal support and the opposing longitudinal support are adjacent the upper leg on essentially opposite sides of the upper leg, the lower longitudinal support and the opposing lower longitudinal support are adjacent the lower leg and on essentially opposite sides of the lower leg, and the medial central joint and opposing central joint are adjacent the knee and on opposite sides of the knee. At least one strap is connected to the upper longitudinal support and the opposing upper longitudinal support and/or to the lower longitudinal support and the opposing lower longitudinal support with sufficient tension to bendably deform the upper longitudinal support and/or the lower longitudinal support at the offset hinge into close fitting conformance with the upper leg and/or the lower leg. In accordance with one embodiment, the frame assembly is force neutral with respect to the leg when the knee brace is placed on the leg and before connecting the at least one strap.

The present invention will be further understood from the drawings and the following detailed description.

DESCRIPTION OF PREFERRED EMBODIMENTS

There are a number of relative terms defined below which are used in the following description to distinguish various elements of the orthopedic brace of the present invention from one another, but which are not to be construed as limiting the scope of the invention. The relative terms "medial" and "lateral" characterize certain elements of the orthopedic brace and, in particular, describe the relative proximity of the given element to the central longitudinal axis of the body of the user when the orthopedic brace is secured thereto. A "medial" element is closer to the central longitudinal axis of the body, while a "lateral" element is further from the central longitudinal axis of the body.

The terms "proximal" and "distal" characterize certain elements of the orthopedic brace, which are aligned with the longitudinal axis of the orthopedic brace. The terms describe the relative proximity of the given element to the central joint of the orthopedic brace. A "proximal" element is closer to the central joint of the orthopedic brace, while a "distal" element is further from the central joint of the orthopedic brace. The terms "upper" and "lower" likewise characterize certain elements of the orthopedic brace, which are aligned with the longitudinal axis of the orthopedic brace. However, the terms describe the position of the given element as being either above or below a horizontal plane running through the central joint of the orthopedic brace. In particular, an "upper" element is above the horizontal plane running through the central joint of the orthopedic brace, while a "lower" element is below the horizontal plane running through the central joint of the orthopedic brace.

The relative terms "posterior" and "anterior" characterize certain elements of the orthopedic brace and, in particular, describe the orientation of the given element relative to the central longitudinal axis of the body of the user when the orthopedic brace is secured thereto. A "posterior" element is positioned behind the central longitudinal axis of the body in correspondence with the posterior of the body, while an "anterior" element is positioned in front of the central longitudinal axis of the body in correspondence with the anterior of the body.

Figure 1:
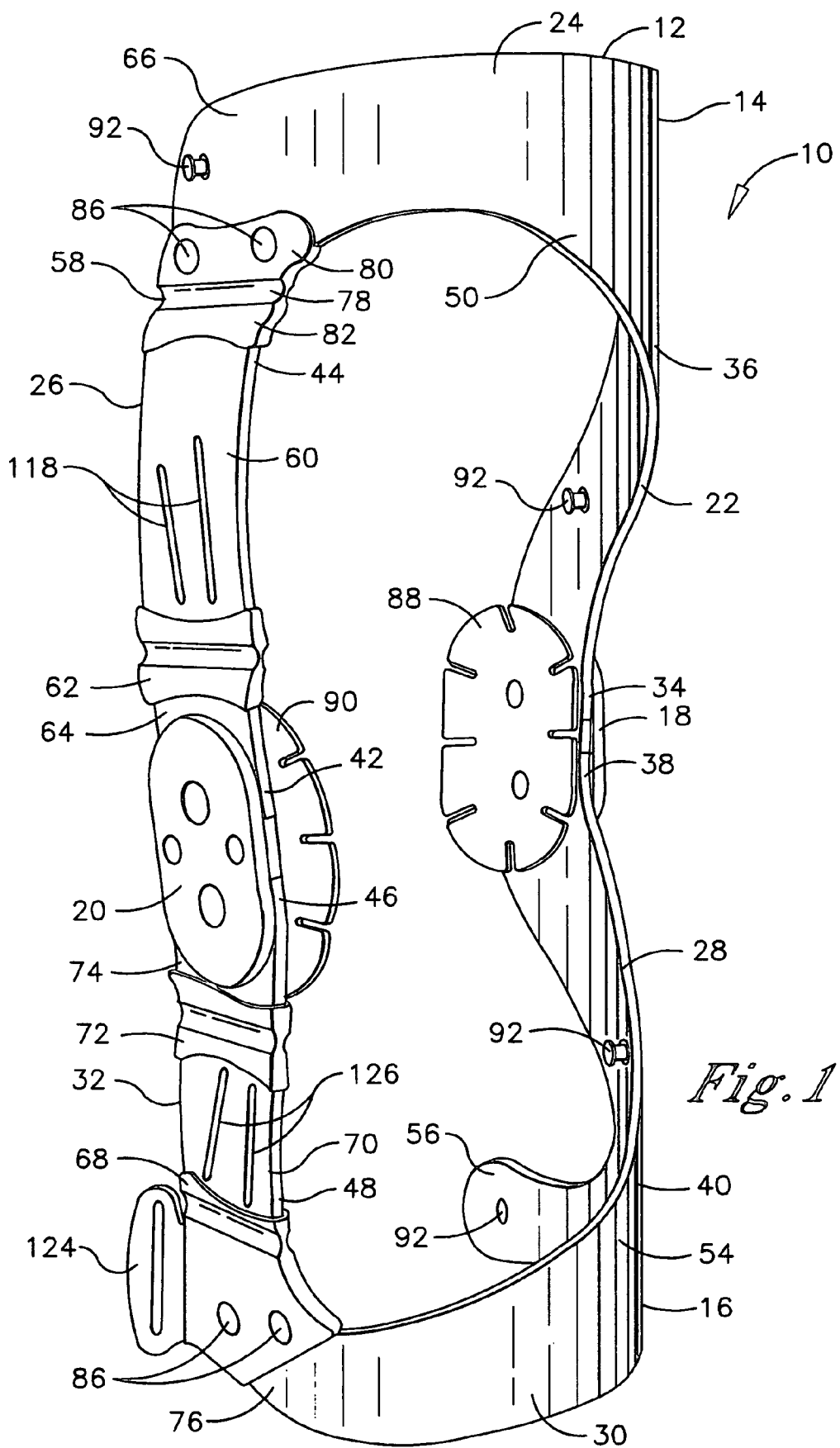
FIG. 1 is a front perspective view of a frame for an orthopedic brace of the present invention, wherein the frame is in a position of full extension.
Figure 2:
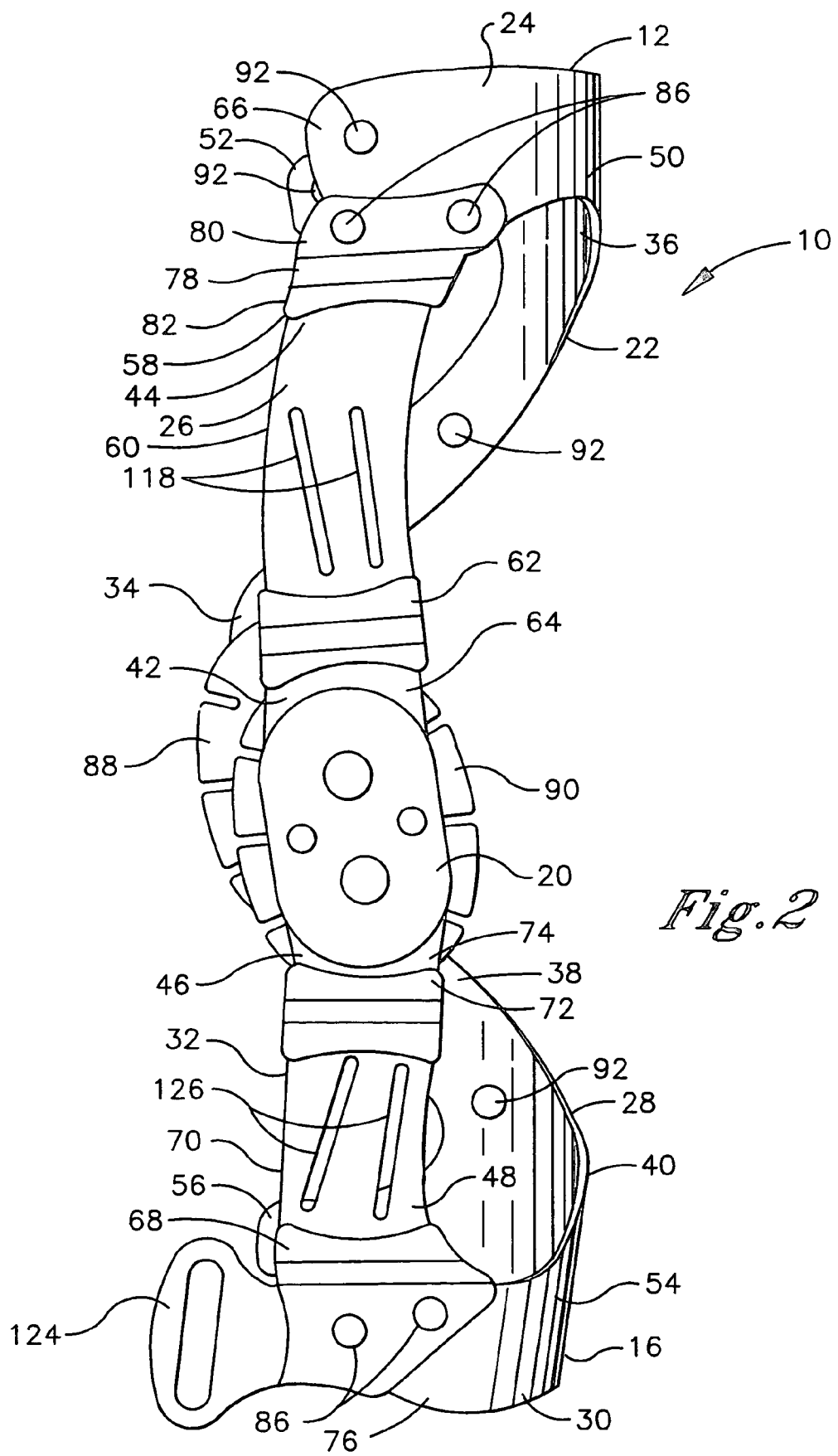
FIG. 2 is a medial elevational view of the frame of FIG. 1, wherein the frame is in a position of full extension.
Figure 3:
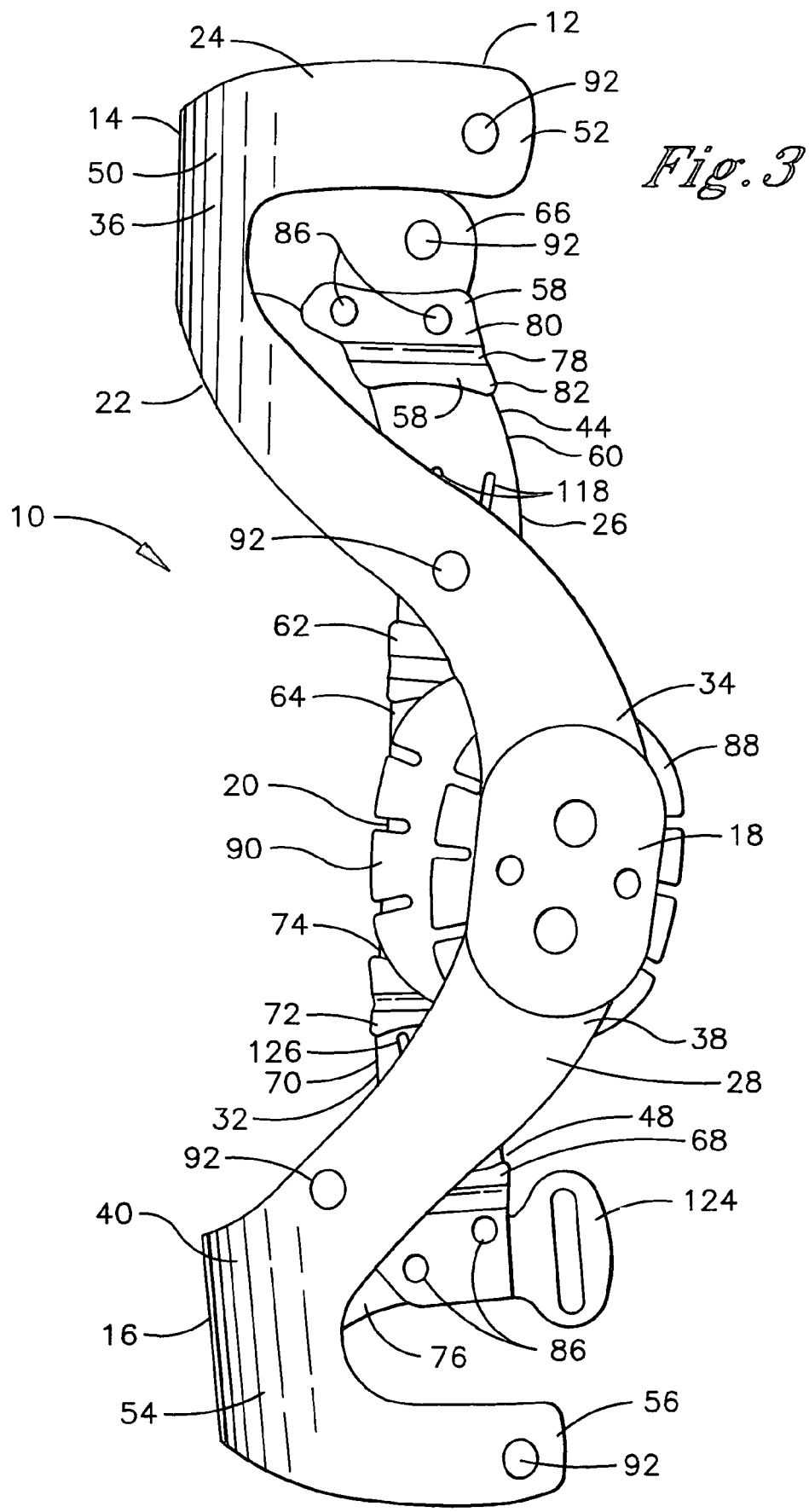
FIG. 3 is a lateral elevational view of the frame of FIG. 1, wherein the frame is in a position of full extension.

Referring initially to FIGS. 1-3, an orthopedic brace is shown and generally designated 10. For purposes of illustration, the orthopedic brace 10 is a knee brace configured for securing to a left leg of a user. However, it is readily apparent to the skilled artisan from the teaching provided hereafter that the orthopedic brace of the present invention can be adapted for securing to other parts of the body to treat skeletal joints apart from the knee.

The orthopedic brace 10 comprises a frame 12, padding, and a plurality of straps and releasable strap retainers. Only the frame 12 is shown in FIG. 1-3, while the padding, straps, and releasable strap retainers are omitted for clarity. For purposes of identifying the structural members of the frame 12 below, the frame 12 is conceptually bisected by a horizontal reference plane into an upper half and a lower half while in a position of full extension and is also conceptually bisected by a vertical reference plane into a lateral half and a medial half. Bisecting the frame 12 in this manner further subdivides the frame 12 into a lateral upper quadrant, a medial upper quadrant, a lateral lower quadrant, and a medial lower quadrant. These conceptual divisions provide a nomenclature system for the below-recited structural members of the frame 12. Thus, a structural member which resides essentially entirely in one quadrant is referenced to that quadrant. A structural member which resides in more than one quadrant, but resides essentially entirely in one half, is referenced to that half.

The frame 12 includes an upper frame assembly 14, a lower frame assembly 16, a lateral central joint 18, and a medial central joint 20. The upper frame assembly 14 comprises in combination a lateral upper longitudinal support 22, an upper cuff 24, and a medial upper longitudinal support 26. The lower frame assembly 16 similarly comprises in combination a lateral lower longitudinal support 28, a lower cuff 30, and a medial lower longitudinal support 32. The lateral upper longitudinal support 22, lateral central joint 18, and lateral lower longitudinal support 28 in serial combination are termed a lateral frame assembly and the medial upper longitudinal support 26, medial central joint 20, and medial lower longitudinal support 32 in serial combination are termed a medial frame assembly The upper and lower frame assemblies 14, 16 are connected to one another by the lateral and medial central joints 18, 20. In particular, the lateral central joint 18 effects lateral connection of the upper and lower frame assemblies 14, 16 in cooperation with the lateral upper and lower longitudinal supports 22, 28. The lateral upper longitudinal support 22 is an elongate arm having a proximal end 34 and a distal end 36 and the lateral lower longitudinal support 28 is similarly constructed, having a proximal end 38 and a distal end 40. The proximal ends 34, 38 of the lateral upper and lower longitudinal supports 22, 28, respectively, are both specifically configured to cooperatively engage one another and to engage the lateral central joint 18. The proximal end 34 of the lateral upper longitudinal support 22 extends from the lateral central joint 18 in a first direction having an upward component and the proximal end 38 of the lateral lower longitudinal support 28 extends from the lateral central joint 18 in a second direction having a downward component.

The lateral central joint 18 is preferably a rotational hinge, which rotationally connects the lateral upper and lower longitudinal supports 22, 28. The proximal ends 34, 38 of the lateral upper and lower longitudinal supports 22, 28, respectively, have an orientation which is essentially perpendicular to the axis of rotation of the lateral central joint 18. The lateral central joint 18 enables rotational displacement of the lateral upper and lower longitudinal supports 22, 28 about the lateral central joint 18 between positions of extension and flexion.

Details of the structure and operation of a representative rotational hinge having utility as the lateral central joint 18 in the orthopedic brace 10 are disclosed in U.S. Pat. No. 5,772,618, which is incorporated herein by reference. However, it is understood that the lateral central joint is not limited to any one specific construction or type of rotational hinge. Thus, most conventional rotational hinges for orthopedic braces, which enable rotation of an upper arm and/or a lower arm about the rotational hinge, can alternatively be employed as the lateral central joint of the present orthopedic brace. Exemplary additional prior art hinges are disclosed in U.S. Pat. Nos. 401,933; 4,481,941; 5,672,152; and 5,827,208. In accordance with a preferred embodiment, the lateral central joint 18 is essentially rigid (i.e., inflexible) in the mediolateral direction (i.e., side-to-side). In accordance with an alternate embodiment the lateral central joint 18 is essentially flexible in the mediolateral direction.

The medial central joint 20 effects medial connection of the upper and lower frame assemblies 14, 16 in cooperation with the medial upper and lower longitudinal supports 26, 32. The medial upper longitudinal support 26 has a proximal end 42 and a distal end 44 and the medial lower longitudinal support 32 similarly has a proximal end 46 and a distal end 48. The proximal ends 42, 46 of the medial upper and lower longitudinal supports 26, 32, respectively, are both specifically configured to cooperatively engage one another and to engage the medial central joint 20. The proximal end 42 of the medial upper longitudinal support 26 extends from the medial central joint 20 in the same first direction as the proximal end 34 of the lateral upper longitudinal support 22 and the proximal end 46 of the medial lower longitudinal support 32 extends from the medial central joint 20 in the same second direction as the proximal end 38 of the lateral lower longitudinal support 28.

The medial central joint 20 is preferably a rotational hinge, which rotationally connects the medial upper and lower longitudinal supports 26, 32, and is more preferably the same type of rotational hinge as the lateral central joint 18. The medial upper and lower longitudinal supports 26, 32 have an orientation which is essentially perpendicular to the axis of rotation of the medial central joint 20. The medial central joint 20 enables rotational displacement of the medial upper and lower longitudinal supports 26, 32 about the medial central joint 20 between positions of extension and flexion in essentially the same manner as the lateral central joint 18. In accordance with a preferred embodiment, the medial central joint 20 is essentially rigid in the mediolateral direction. In accordance with an alternate embodiment the medial central joint 20 is essentially flexible in the mediolateral direction. When the orthopedic brace 10 is secured to the leg of a user, the medial central joint 20, in cooperation with the lateral central joint 18, correspondingly enables extension and flexion rotation of the upper and lower leg about the knee.

The upper cuff 24 extends between the distal end 36 of the lateral upper longitudinal support 22 and the distal end 44 of the medial upper longitudinal support 26. The upper cuff 24 has an orientation which is essentially parallel to the axis of rotation of the lateral and medial central joints 18, 20. The lower cuff 30 extends between the distal end 40 of the lateral lower longitudinal support 28 and the distal end 48 of the medial lower longitudinal support 32. The lower cuff 30 likewise has an orientation which is essentially parallel to the axis of rotation of the lateral and medial central joints 18, 20.

The lateral upper longitudinal support 22 is characterized as a relatively rigid member. The rigidity (or conversely the flexibility) of any member of the orthopedic brace 10 is generally a function of both the material from which the member is constructed and the resulting geometry of the member. Thus, a material such as aluminum, which is commonly deemed rigid, can be rendered flexible by configuring the material in a particular geometry in a manner apparent to the skilled artisan. Conversely, a material such as nylon, which is commonly deemed flexible, can be rendered rigid by configuring the material in a particular geometry in a manner apparent to the skilled artisan.

The lateral upper longitudinal support 22 is preferably constructed from a unitary piece of material, such as a piece of aluminum, and configured in a geometry which provides the lateral upper longitudinal support 22 with a relatively high and essentially uniform degree of rigidity along the entirety of its length. The lateral upper longitudinal support 22 is preferably rigidly connected to the upper cuff 24 by rigid fixed attachment thereto. The upper cuff 24 is likewise preferably constructed from a material and configured in a geometry which provides the upper cuff 24 with a relatively high and essentially uniform degree of rigidity. Rigid fixed attachment of the lateral upper longitudinal support 22 and upper cuff 24 is preferably effected by integrally forming the upper cuff 24 and lateral upper longitudinal support 22 from a single piece of uniform material. For example, the upper cuff 24 and lateral upper longitudinal support 22 can be integrally formed from a single piece of aluminum as described in U.S. Pat. No. 5,782,780, incorporated herein by reference.

The lateral lower longitudinal support 28 is likewise a relatively rigid member preferably constructed from a unitary piece of material, such as a piece of aluminum, which provides the lateral lower longitudinal support 28 with a relatively high and essentially uniform degree of rigidity along the entirety of its length. The lateral lower longitudinal support 28 is preferably rigidly connected to the lower cuff 30 by rigid fixed attachment thereto. The lower cuff 30 is likewise preferably constructed from a material and configured in a geometry which provides the lower cuff 30 with a relatively high and essentially uniform degree of rigidity. Rigid fixed attachment of the lateral lower longitudinal support 28 and lower cuff 30 is preferably effected by integrally forming the lower cuff 30 and lateral lower longitudinal support 28 from a single piece of uniform material, such as aluminum, in the same manner as the upper cuff 24 and lateral upper longitudinal support 22.

The lateral upper longitudinal support 22 and the upper cuff 24 each has an arcuate configuration which enables conformance to the contours of the anterior upper leg. The lateral lower longitudinal support 28 and lower cuff 30 similarly each has an arcuate configuration which enables conformance thereof to the contours of the anterior lower leg. The distal end 36 of the lateral upper longitudinal support 22 merges into an intermediate point 50 on the upper cuff 24 near the lateral end 52 of the upper cuff 24. The distal end 40 of the lateral lower longitudinal support 28 similarly merges into an intermediate point 54 on the lower cuff 30 near the lateral end 56 of the lower cuff 30.

Whereas the lateral upper longitudinal support 22 has a uniform and rigid construction, the medial upper longitudinal support 26 has a segmented construction which provides the medial upper longitudinal support 26 with a non-uniform degree of rigidity (and conversely flexibility) along its length. In particular, the medial upper longitudinal support 26 is constructed in four segments, namely, an upper distal offset hinge 58, an upper sidebar 60, an upper proximal offset hinge 62, and an upper central connector 64. The upper sidebar 60 and upper central connector 64 are flexibly connected to one another by the upper proximal offset hinge 62, which extends between and is fixably attached to the upper sidebar 60 and upper central connector 64. The upper distal offset hinge 58 flexibly connects the upper sidebar 60 with the medial end 66 of the upper cuff 24.

The upper proximal offset hinge 62 is characterized as having a lower degree of rigidity (and conversely a higher degree of flexibility) than either the upper sidebar 60 or the upper central connector 64. The upper proximal offset hinge 62 is termed a "hinge" because it has a sufficient degree of flexibility to enable manual displacement of the more rigid upper sidebar 60 relative to the more rigid upper central connector 64 about the less rigid upper proximal offset hinge 62 in the mediolateral direction or in a twisting direction. As such, a hinge is defined herein as an essentially flexible connective member which extends between and connects two separate, and preferably more rigid, members. The upper proximal offset hinge 62 is further characterized as an "offset hinge" because it enables the two more rigid members which it connects to assume a non-linear orientation with respect to one another, thereby creating an offset angle between them when they are displaced about the offset hinge.

The upper distal offset hinge 58 is similarly characterized as having a lower degree of rigidity (and conversely a higher degree of flexibility) than either the upper sidebar 60 or the upper cuff 24. The upper distal offset hinge 58 is termed a "hinge" because it has a sufficient degree of flexibility to enable manual displacement of the more rigid upper sidebar 60 relative to the more rigid upper cuff 24 about the less rigid upper distal offset hinge 58 in the mediolateral direction or in a twisting direction.

The medial lower longitudinal support 32 has essentially the same construction as the medial upper longitudinal support 26. Thus, the medial lower longitudinal support 32 has four segments, namely, a lower distal offset hinge 68, a lower sidebar 70, a lower proximal offset hinge 72, and a lower central connector 74. The lower sidebar 70 and lower central connector 74 are flexibly connected to one another by the lower proximal offset hinge 72, which extends between and is fixably attached to the lower sidebar 70 and lower central connector 74. The lower distal offset hinge 68 flexibly connects the lower sidebar 70 with the medial end 76 of the lower cuff 30.

The lower proximal offset hinge 72 has a lower degree of rigidity (and conversely a higher degree of flexibility) than either the lower sidebar 70 or the lower central connector 74. As such, the lower proximal offset hinge 72 has a sufficient degree of flexibility to enable manual displacement of the more rigid lower sidebar 70 relative to the more rigid lower central connector 74 about the less rigid lower proximal offset hinge 72 in the mediolateral direction or in a twisting direction.

The lower distal offset hinge 68 has a lower degree of rigidity (and conversely a higher degree of flexibility) than either the lower sidebar 70 or the lower cuff 30. As such, the lower distal offset hinge 68 has a sufficient degree of flexibility to enable manual displacement of the more rigid lower sidebar 70 relative to the more rigid lower cuff 30 about the less rigid lower distal offset hinge 68 in the mediolateral direction or in a twisting direction.

The upper and lower central connectors 64, 74 are each preferably constructed from a unitary piece of material, such as a piece of aluminum, and configured in a geometry, which provides the upper and lower central connectors 64, 74 with a relatively high and essentially uniform degree of rigidity, preferably essentially equal to the rigidity of the lateral upper and/or lower longitudinal supports 22, 28. The upper and lower sidebars 60, 70 can likewise each be constructed from a unitary piece of material, such as a piece of aluminum or alternatively a molded piece of nylon, and configured in a geometry which provides the upper and lower sidebars 60, 70 with a relatively high and essentially uniform degree of rigidity, preferably essentially equal to the rigidity of the upper and lower central connectors 64, 74. The upper and lower sidebars 60, 70 having this construction are termed rigid sidebars and are highly resistant to deformation by bending in the mediolateral direction or to deformation by twisting. Therefore, the primary location of variance in the degree of rigidity of the medial upper and lower longitudinal supports 26, 32 is across the upper and lower distal and proximal offset hinges 58, 62, 68, 72, respectively.

In accordance with an alternate embodiment, the upper and/or lower sidebars 60, 70 are constructed from a unitary piece of material, such as a molded piece of nylon, and configured in an alternate geometry which provides the upper and lower sidebars 60, 70 with a relatively lower degree of rigidity (and conversely a higher degree of flexibility), which is preferably more flexible than the upper and lower central connectors 64, 74, but substantially less flexible than the offset hinges 58, 62, 68, 72. The upper and lower sidebars 60, 70 having this construction are termed flexible sidebars and are at least somewhat less resistant to deformation by bending in the mediolateral direction and deformation by twisting than rigid sidebars. Therefore, the primary location of variance in the degree of rigidity of the medial upper and lower longitudinal supports 26, 32 in the present embodiment remains across the upper and lower distal and proximal offset hinges 58, 62, 68, 72, respectively. However, there is a lesser secondary location of variance in the degree of rigidity of the medial upper and lower longitudinal supports 26, 32 across the upper and lower sidebars 60, 70, respectively.

The upper and lower sidebars 60, 70, whether rigid or flexible, have a relatively flat planar construction in the present embodiment. It is alternately within the scope of the present invention to contour the construction of the upper and/or lower sidebar 60, 70 to more closely conform the upper and/or lower sidebar 60, 70 to the contours of the leg of a user to which the orthopedic brace 10 is to be secured. For example, it may be desirable to contour the upper sidebar 60 as well as the lateral upper longitudinal support 22 at an angle toward one another as they approach the lateral and medial central joints 18, 20, respectively, in correspondence with the taper of the upper leg as it approaches the knee. It may similarly be desirable to contour the lower sidebar 70 as well as the lateral lower longitudinal support 28 at an angle toward one another as they approach the lateral and medial central joints 18, 20, respectively, in correspondence with the taper of the lower leg as it approaches the knee.

The offset hinges 58, 62, 68, 72 each preferably has essentially the same general construction. Accordingly, the construction of the upper distal offset hinge 58 is described below, it being understood, unless stated otherwise, that this description applies generally to the remaining offset hinges 62, 68, 72.

The upper distal offset hinge 58 is preferably constructed from a unitary piece of material, which is formed into an integrated multi-sectional configuration. In particular, the upper distal offset hinge 58 has three integrally-formed sections, namely, a deformation section 78, a distal attachment section 80, and a proximal attachment section 82. The deformation section 78 is a location on the upper distal offset hinge 58 between the distal and proximal attachment sections 80, 82 configured in a geometry, which provides the upper distal offset hinge 58 with a relatively high degree of flexibility, i.e., preferably substantially higher than the flexibility the remaining members of the frame 12. In particular, the deformation section 78 is preferably constructed to be capable of bendable deformation in the mediolateral direction or rotational deformation in a twisting direction when a routine displacement force is applied to the upper distal offset hinge 58, while being relatively non-stretchable.

The deformation section 78 is further constructed to resist loss of strength and, in particular, to resist tearing, breaking, or other permanent deformation, even after prolonged and repeated bending without substantially impairing elastic bending under routine forces. Materials having utility herein as an offset hinge, which can exhibit such desirable flexibility characteristics when properly configured include natural or synthetic elastomers, plastics, fiberglass, composites, fabrics, leather, metals and the like. A preferred material is a molded plastic and more preferably a molded nylon. An alternate preferred material is a high-strength plastic sheeting. A hinge which has the above-described construction of the upper distal offset hinge 58 is commonly termed a "living hinge". However, it is understood that the present invention is not limited to the present specific embodiment of an offset hinge, but additionally contemplates the use of alternate hinges which enable manual displacement of the more rigid members relative to one another in the mediolateral direction or in a twisting direction.

The distal attachment section 80 is a location on the upper distal offset hinge 58 which is configured for fixed attachment to the distal adjacent member of the frame 12 above the upper distal offset hinge 58. In the case of the upper distal offset hinge 58, the distal adjacent member is the upper cuff 24 and the distal attachment section 80 is attached to the medial end 66 of the upper cuff 24. The proximal attachment section 82 is a location on the upper distal offset hinge 58 which is configured for fixed attachment to the proximal adjacent member of the frame 12 below the upper distal offset hinge 58. In the case of the upper distal offset hinge 58, the proximal adjacent member is the upper sidebar 60 and the proximal attachment section 82 is attached to the distal end of the upper sidebar 60 (which corresponds to the distal end 44 of the medial upper longitudinal support 26).

The specific case shown in FIGS. 1 and 2 where the upper distal offset hinge 58 is constructed from molded nylon, and the proximal adjacent member of the frame 12, i.e., the upper sidebar 60, is constructed from aluminum, attachment of the upper distal offset hinge 58 and the upper sidebar 60 is effected by a technique termed overmolding. In accordance with the overmolding technique, a plurality of holes or slots (not shown) are provided in the distal end 44 of the upper sidebar 60. While the upper distal offset hinge 58 is being formed in a mold from a hot fluid plastic, the distal end 44 of the upper side bar 60 is inserted into the mold. The fluid plastic envelopes the distal end 44 and flows into the holes or slots therein to form the proximal attachment section 82 of the upper distal offset hinge 58. When the plastic hardens, the distal end 44 of the upper sidebar 60 and the upper distal offset hinge 58 are removed from the mold in a condition of fixed attachment to one another. It is noted that the deformation section 78 of the upper distal offset hinge 58 has a narrower cross-section than the proximal attachment section 82 (and correspondingly the distal attachment section 80), which provides the deformation section 78 with desirable flexibility characteristics.

Fasteners provide an alternate technique for attachment of the upper distal offset hinge 58 to an adjacent member of the frame 12. Fasteners have general utility as attachment means regardless of whether the upper distal offset hinge 58 and/or the adjacent member are formed from molded nylon, metal or any other of the above-recited materials. Preferred fasteners are rivets which extend through the distal or proximal attachment section 80, 82 of the upper distal offset hinge 58 and the distal or proximal adjacent member, respectively, to effect attachment thereof. In the specific case shown in FIGS. 1 and 2, attachment of the upper distal offset hinge 58 and the upper cuff 24 is effected by conventional rivets 86. In particular, the rivets 86 extend through the distal attachment section 80 of the upper distal offset hinge 58 and the medial end 66 of the upper cuff 24 to effect attachment thereof.

FIGS. 1 and 2 further show attachment of the upper proximal offset hinge 62 to both the upper sidebar 60 and upper central connector 64 by overmolding. Likewise, attachment of the lower proximal offset hinge 72 to both the lower sidebar 70 and lower central connector 74 is effected by overmolding. Attachment of the lower distal offset hinge 68 and the lower sidebar 70 is effected by overmolding while attachment of the lower distal offset hinge 68 and the lower cuff 30 is effected by rivets 86.

It is understood that the specific means of attaching designated offset hinges to corresponding adjacent members of the frame 12 are recited above by way of example and are not intended to limit the present invention. Thus, it is within the scope of the present invention to alternately effect attachment of the lower distal offset hinge 68 and the lower sidebar 70 by rivets 86, alternately effect attachment of the lower proximal offset hinge 72 and the lower sidebar 70 by rivets 86, alternately effect attachment of the lower proximal offset hinge 72 and the lower central connector 74 by rivets 86, alternately effect attachment of the lower distal offset hinge 68 and the lower cuff 30 by overmolding, alternately effect attachment of the upper distal offset hinge 58 and the upper sidebar 60 by rivets 86, alternately effect attachment of the upper proximal offset hinge 62 and the upper sidebar 60 by rivets 86, alternately effect attachment of the upper proximal offset hinge 62 and the upper central connector 64 by rivets 86, or alternately effect attachment of the upper distal offset hinge 58 and the upper cuff 24 by overmolding.

In accordance with an alternate embodiment not shown, either or both sidebars 60, 70 and the adjacent distal and/or proximal offset hinge 58, 62, 68, 72 are integrally constructed from a unitary piece of material, such as a molded piece of nylon, wherein the sidebar 60, 70 is either rigid or flexible. In all cases, however, the sidebar 60, 70 has a higher degree of rigidity (and conversely a lower degree of flexibility) than the adjacent offset hinge 58, 62, 68, 72.

In accordance with another alternate embodiment not shown, the upper sidebar 60 is constructed from aluminum as described above. The upper distal and proximal offset hinges 58, 62 are integrally constructed from a unitary piece of material, such as a molded piece of nylon. The upper sidebar 60 is encased within the unitary piece of material on either side of the upper distal and proximal offset hinges 58, 62, by means such as overmolding the entire upper sidebar 60, to effect attachment of the upper sidebar 60 with the upper distal and proximal offset hinges 58, 62, respectively. The lower sidebar 70 can likewise be constructed from aluminum, while the lower distal and proximal offset hinges 68, 72 are integrally constructed from a unitary piece of material, such as a molded piece of nylon. The lower sidebar 70 is encased within the unitary piece of material on either side of the lower distal and proximal offset hinges 68, 72 to effect attachment of the lower sidebar 70 with the lower distal and proximal offset hinges 68, 72, respectively.

In accordance with the embodiment of FIGS. 1-3, the frame 12 additionally includes a lateral condyle cup 88, a medial condyle cup 90, and a plurality of strap anchors 92. The lateral and medial condyle cups 88, 90 are associated with the lateral and medial central joints 18, 20, respectively, and each has an essentially identical concave flexible plastic construction. The lateral and medial condyle cups 88, 90 are fastened to the rigid inner surfaces of the lateral and medial central joints 18, 20, respectively, and function as stiffened supports for associated condyle pads, which are described below. Each strap anchor 92 is a male coupling for a female coupling of a strap retainer (not shown in FIGS. 1-3). The construction and function of strap anchors 96 and strap retainers, which have utility herein are disclosed in U.S. Patent Publication Nos. 2003-0176823 and 2003-0176824 incorporated herein by reference.

Figure 4:
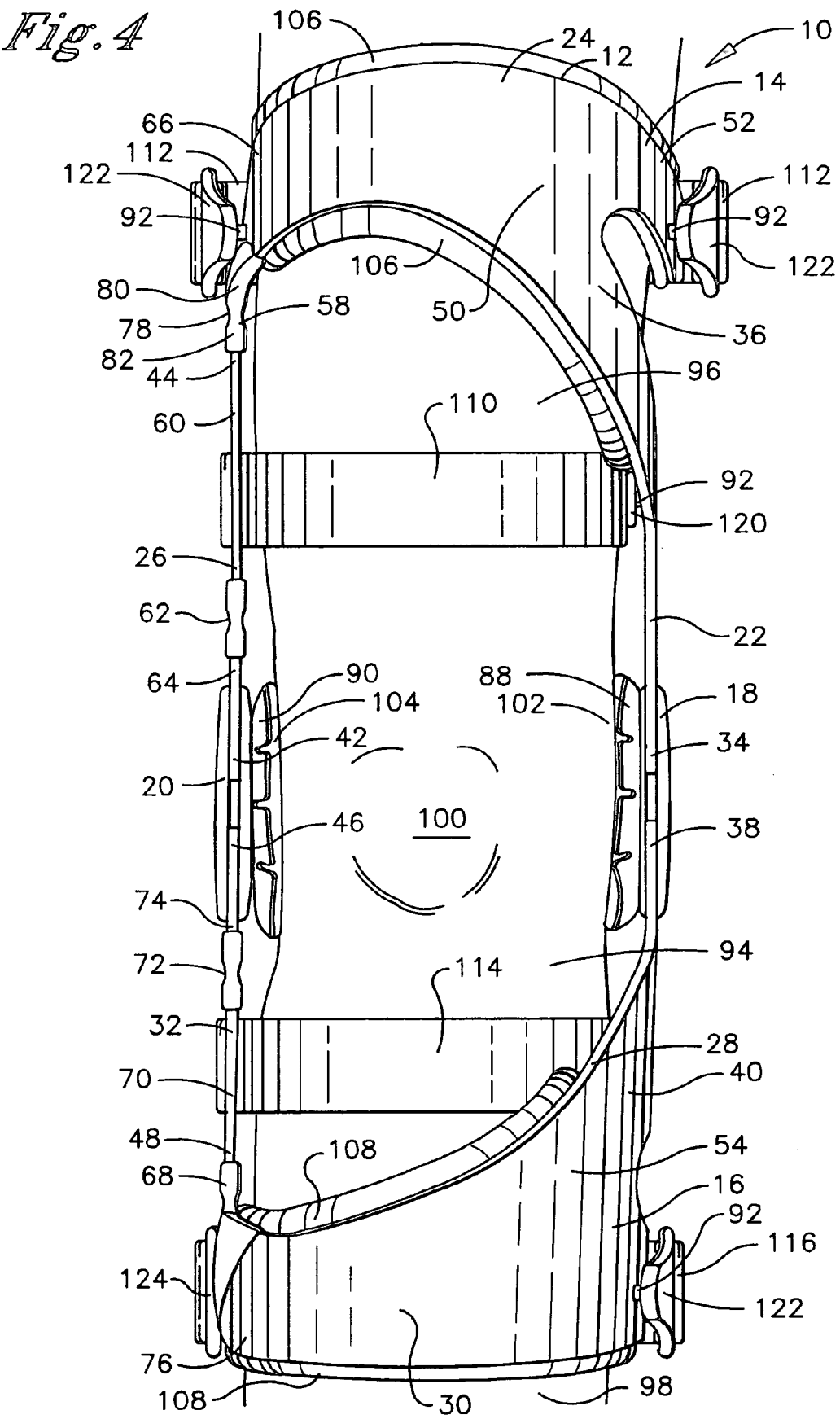
FIG. 4 is a front elevational view of an orthopedic brace having the frame of FIG. 1, wherein the orthopedic brace is secured to a leg of a user in a position of full extension.
Figure 5:
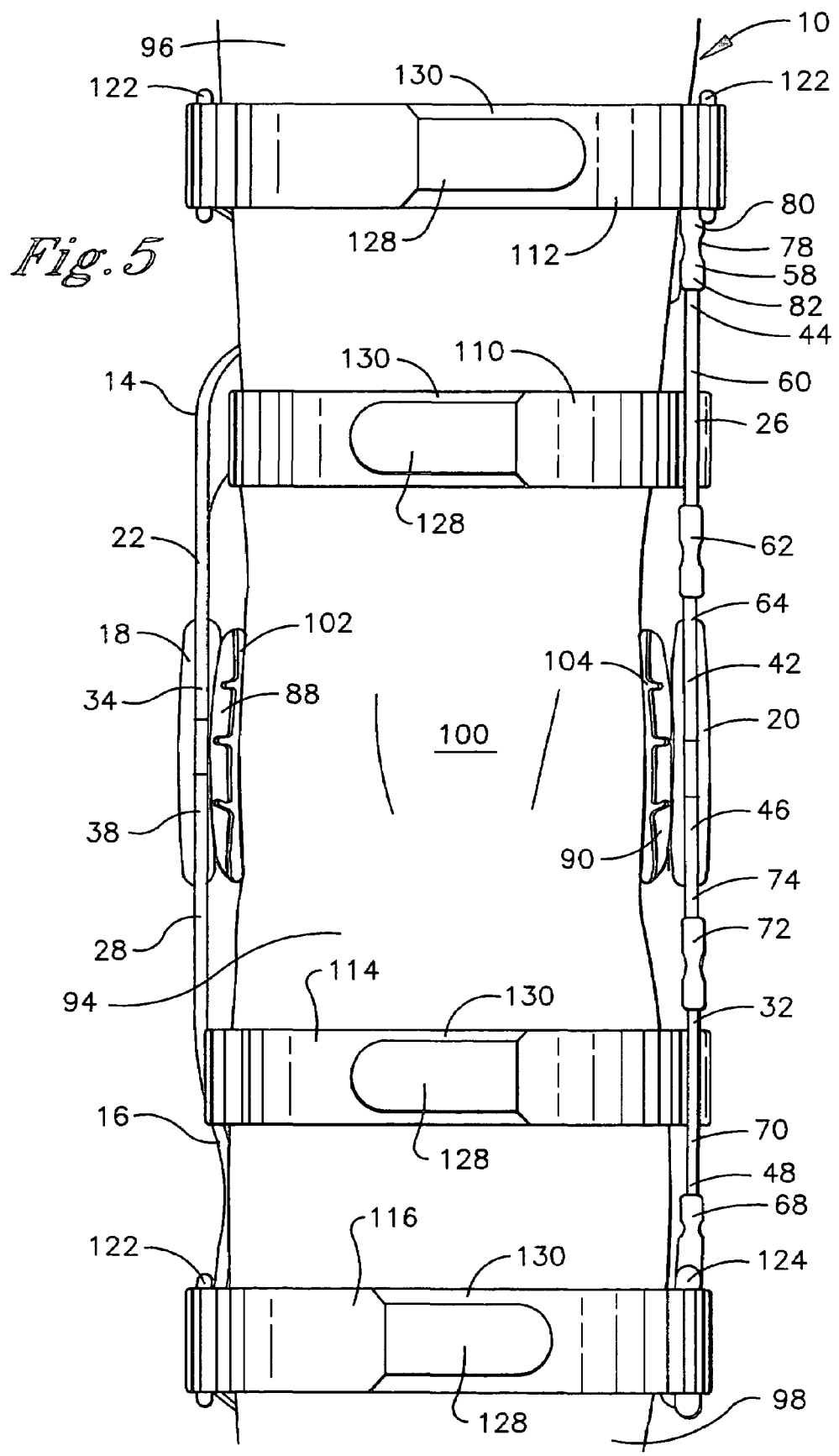
FIG. 5 is a rear elevational view of the orthopedic brace of FIG. 4 secured to a leg of a user in a position of full extension.
Figure 6:
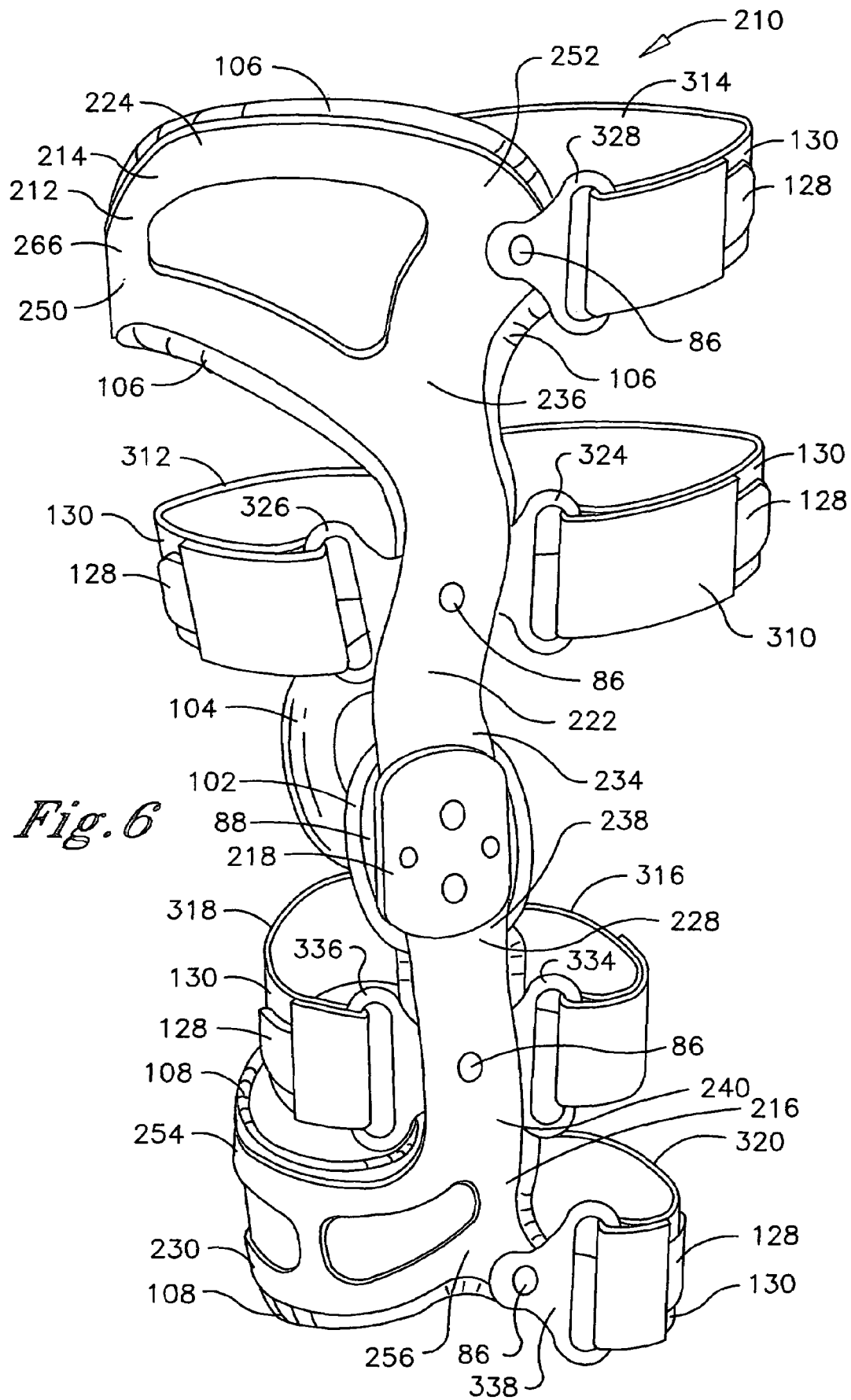
FIG. 6 is a medial elevational view of an alternate embodiment an orthopedic brace of the present invention, wherein the brace is in a position of full extension.
Figure 7:
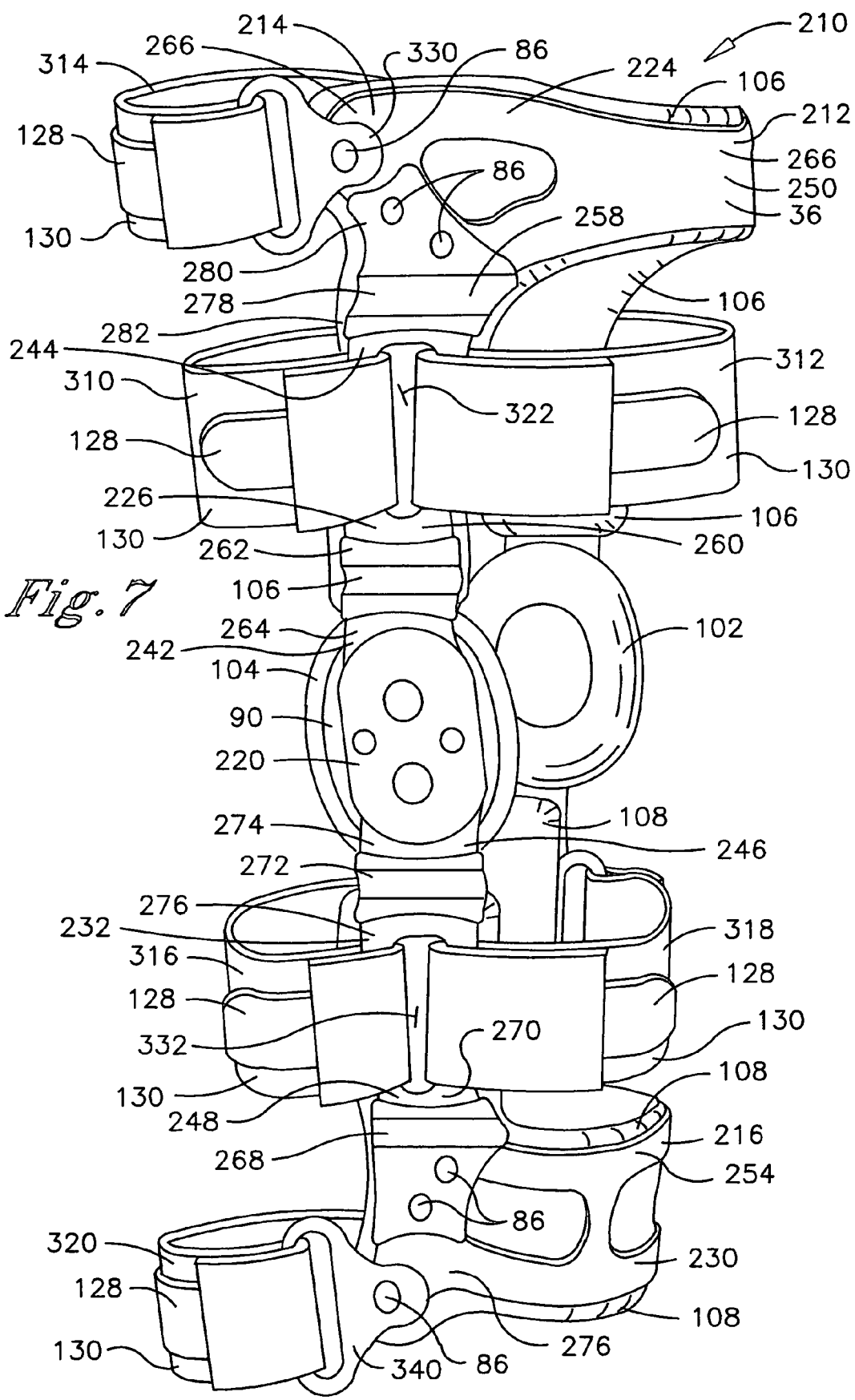
FIG. 7 is a lateral elevational view of the orthopedic brace of FIG. 6, wherein the brace is in a position of full extension.
Figure 8:
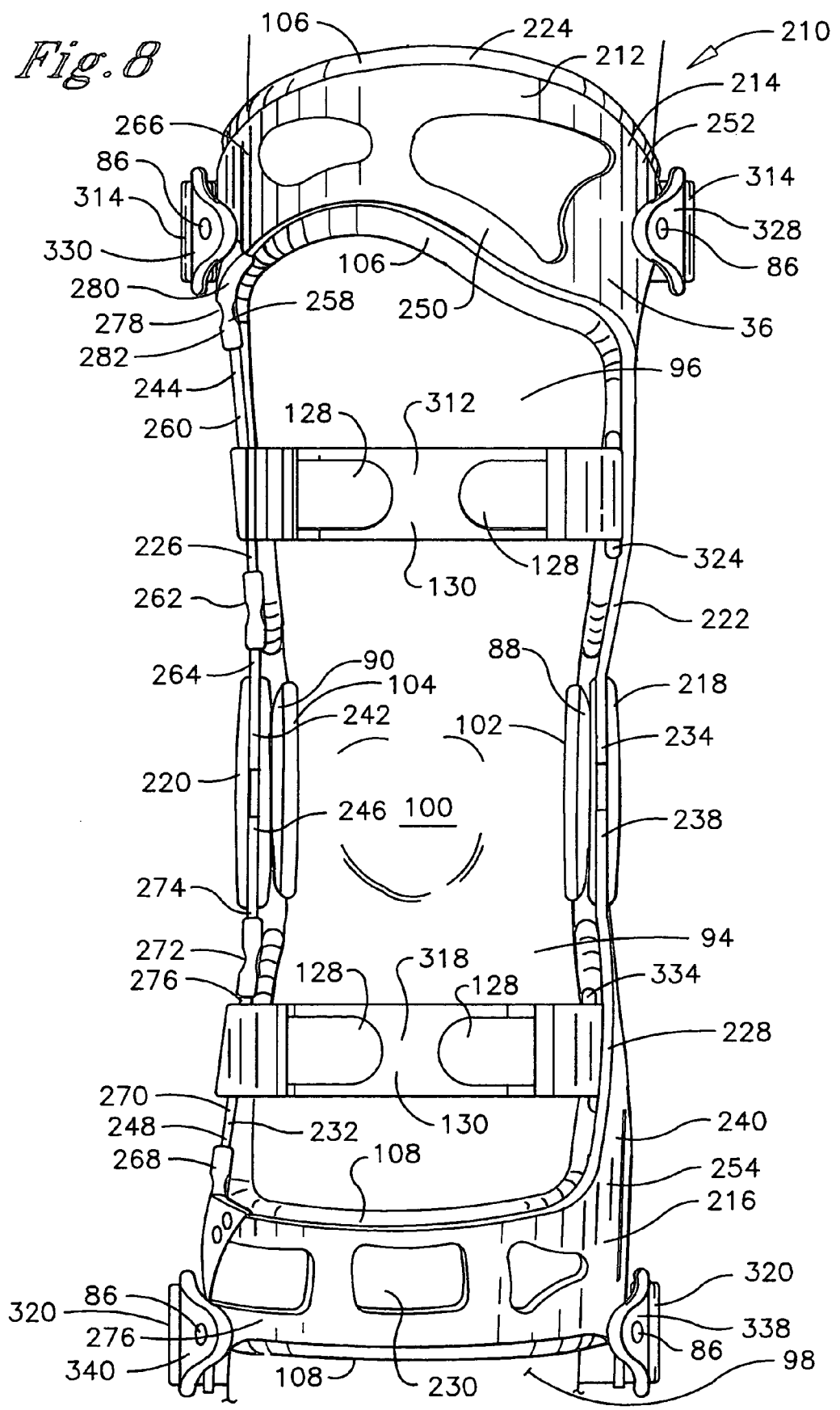
FIG. 8 is a front elevational view of the orthopedic brace of FIG. 6 secured to a leg of a user in a position of full extension.
Figure 9:
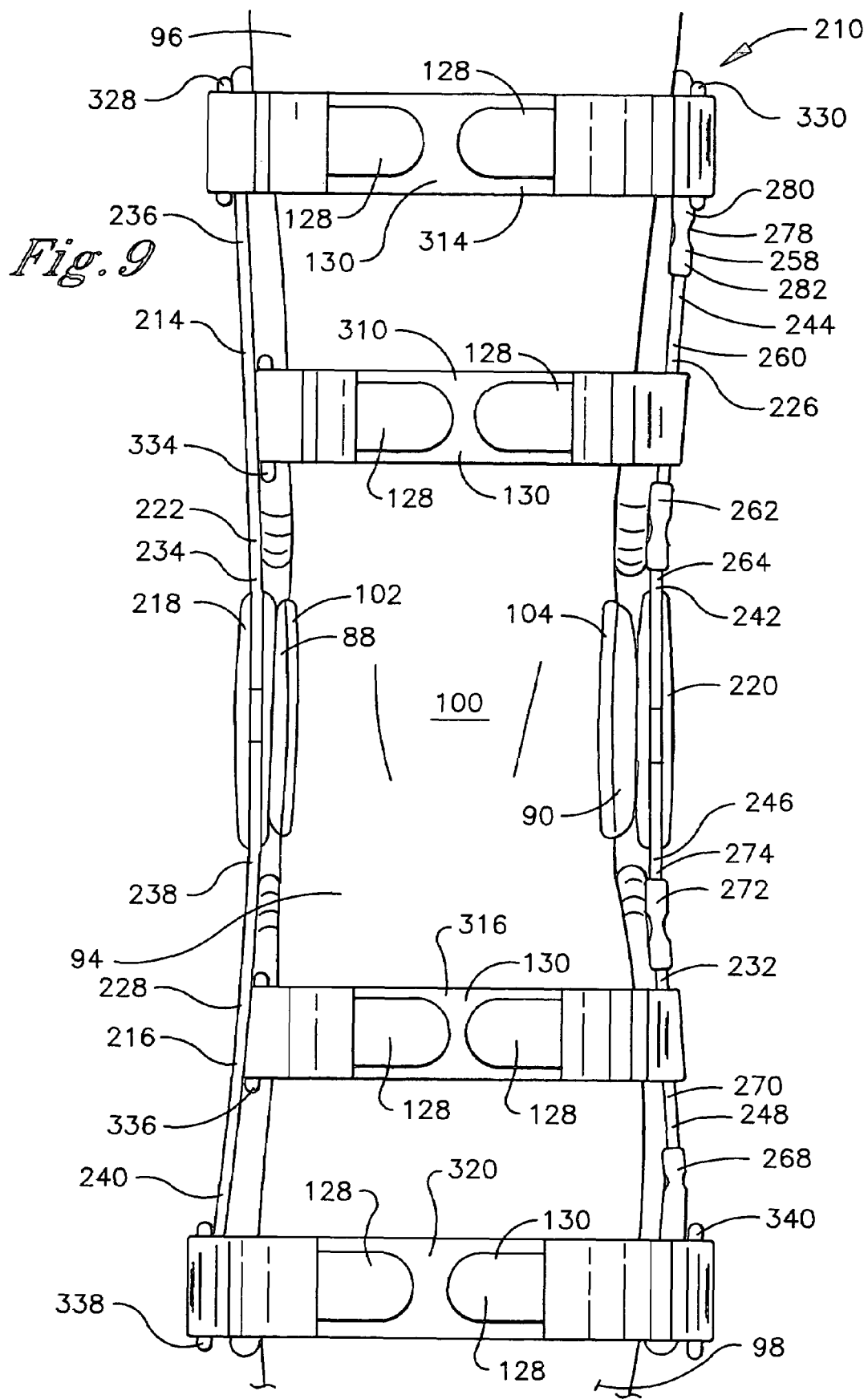
FIG. 9 is a rear elevational view of the orthopedic brace of FIG. 6 secured to a leg of a user in a position of full extension.

Full utility of the orthopedic brace 10 is achieved when the orthopedic brace 10 is secured to the leg of a user. Referring additionally to FIGS. 4 and 5, the orthopedic brace 10 is secured to a left leg 94, which is characterized as having an upper leg 96, a lower leg 98, and a knee 100 rotationally connecting the upper and lower legs 96, 98. It will be apparent to the skilled artisan that the orthopedic brace 10 is likewise adaptable for securing to the right leg (not shown) of the user.

When the orthopedic brace 10 is properly secured to the leg 94, the lateral central joint 18 is positioned adjacent to the lateral side of the knee 100 and the medial central joint 20 is positioned adjacent to the medial side of the knee 100. In contrast, the offset hinges 58, 62, 68, 72 are all more distally positioned relative to the knee 100. The lateral upper longitudinal support 22 is positioned essentially adjacent to the lateral side of the upper leg 96 is essentially longitudinally aligned therewith. The medial upper longitudinal support 26 is positioned essentially adjacent to the medial side of the upper leg 96 and is essentially longitudinally aligned therewith. The lateral lower longitudinal support 28 is positioned essentially adjacent to the lateral side of the lower leg 98 and is essentially longitudinally aligned therewith. The medial lower longitudinal support 32 is positioned essentially adjacent to the medial side of the lower leg 98 and is essentially longitudinally aligned therewith.

In addition to the above-described frame 12, the orthopedic brace 10 further comprises a lateral condyle pad 102, a medial condyle pad 104, upper frame padding 106, and lower frame padding 108. The lateral and medial condyle pads 102, 104 are removably fastened to the lateral and medial condyle cups 88, 90, respectively, preferably by conventional hook and loop fasteners ("VELCRO"). The lateral and medial condyle pads 102, 104 each has an essentially identical cloth-covered foam construction, which cushions the user from the rigid lateral and medial central joints, 18, 20, respectively, when the orthopedic brace 10 is secured to the leg of a user. The upper frame padding 106 and lower frame padding 108 are associated with the upper and lower frame assemblies 14, 16, respectively, and are configured in correspondence therewith. The upper frame padding 106 and lower frame padding 108 are removably fastened to the upper and lower frame assemblies 14, 16, respectively, preferably by hook and loop fasteners. The upper frame padding 106 and lower frame padding 108 each has a cloth-covered foam construction, which cushions the user from the upper and lower frame assemblies 14, 16, respectively, when the orthopedic brace 10 is secured to the leg of a user.

The orthopedic brace 10 still further comprises a plurality of securing straps, namely, an upper proximal strap 110, an upper distal strap 112, a lower proximal strap 114, and a lower distal strap 116. The securing straps 110, 112, 114, 116 are each flexible, yet relatively non-stretchable, cloth straps which closely secure the orthopedic brace 10 to the leg 94. In particular, the upper proximal strap 110 is a full circumferential strap which extends around the upper leg 96 proximal to the knee 100 in a complete circular path between the lateral and medial upper longitudinal supports 22, 26. The upper proximal strap 110 is threaded through upper strap slots 118 formed through the medial upper longitudinal support 26 and releasably connected to the lateral upper longitudinal support 26 by a strap attachment assembly of the type disclosed in U.S. Patent Publication No. 2003-0176823, which includes the strap anchor 96 of the frame 12 and a releasable internal strap retainer 120 fixably attached to the upper proximal strap 110.

The upper distal strap 112 is a partial circumferential strap which extends posteriorly around the upper leg 96 distal to the knee 100 in a semi-circular path between the lateral and medial ends 52, 66 of the upper cuff 24. The upper distal strap 112 is releasably connected to the lateral and medial ends 52, 66 of the upper cuff 24 by strap connector assemblies of the type disclosed in U.S. Patent Publication No. 2003-0176824 which each includes the strap anchor 96 of the frame 12 and a releasable external strap retainer 122 releasably attached to the upper distal strap 112.

The lower proximal strap 114 is a full circumferential strap which is essentially the same as the upper proximal strap 110, but which extends around the lower leg 98 proximal to the knee 100 in a complete circular path between the lateral and medial lower longitudinal supports 28, 32. The lower proximal strap 114 is threaded through lower strap slots 126 formed through the medial lower longitudinal support 32 and releasably connected to the lateral lower longitudinal support 28 by the strap attachment assembly of the type recited above.

The lower distal strap 116 is a partial circumferential strap which is essentially the same as the upper distal strap 112, but which extends posteriorly around the lower leg 98 distal to the knee 100 in a semi-circular path between the lateral and medial ends 56, 76 of the lower cuff 30. The lower distal strap 116 is releasably connected to the lateral end 56 of the lower cuff 30 by the strap connector assembly of the type disclosed in U.S. Patent Publication No. 2003-0176824. The lower distal strap 116 is releasably connected to the medial end 76 of the lower cuff 30 by a fixed strap retainer 124, which is integrally formed with the distal attachment section 80 of the lower distal offset hinge 68.

Each securing strap 110, 112, 114, 116 is fitted with first and second releasable fasteners 128, 130, preferably hook and loop fasteners, which enable a strap end having the first fastener 128 to be looped through the upper strap slots 118, releasable external strap retainer 122, fixed strap retainer 124, or lower strap slots 126, doubled back onto the second fastener 130 integral with the strap midsection, and fastened thereto. The user is able to adjust the strap length and strap tension by selection of the point on the second fastener 130 where the first fastener 128 is fastened. Accordingly, each of the securing straps 110, 112, 114, 116 may be tightened or loosened by shortening or lengthening the securing straps 110, 112, 114, 116, enabling the user to adjust the fit of the orthopedic brace 10 to the leg 94 and correspondingly to adjust the degree of support and stability the orthopedic brace 10 provides the knee 100.

It is understood that the specific means of connecting the securing straps to corresponding members of the frame 12 are recited above by way of example and are not intended to limit the present invention. Thus, for example, it is alternately within the scope of the present invention to substitute the fixed strap retainer 124 for the strap connector assembly disclosed in U.S. Patent Publication No. 2003-0176824 or to substitute the strap connector assembly disclosed in U.S. Patent Publication No. 2003-0176824 for the fixed strap retainer 124.

Although not shown, it is within the scope of the present invention to omit the upper and/or lower cuffs 24, 30 from the frame 12 of the orthopedic brace 10. In accordance with this embodiment, a full circumferential strap may be substituted for the respective cuff 24, 30 and the respective distal strap 112, 116. The resulting full circumferential strap and its means of attachment to the distal ends 36, 44 or the distal ends 40, 48 are similar to the proximal straps 110, 114 or distal straps 112, 116. In this case, the distal ends 44, 48 coincide with the distal ends of the upper and lower sidebars 60, 70, respectively. The upper and lower proximal offset hinges 62, 72 remain positioned between the upper sidebar 60 and upper central connector 64 and the lower sidebar 70 and lower central connector 74, respectively. The upper distal offset hinge 58 is inserted in a distal portion of the upper sidebar 60 below the distal end 44 where the circumferential strap is attached and the lower distal offset hinge 68 is inserted in a distal portion of the lower sidebar 70 above the distal end 48 where the circumferential strap is attached.

Referring to FIGS. 6-9, an alternate embodiment of an orthopedic brace is shown and generally designated 210. The orthopedic brace 210 has essentially the same elements as the orthopedic brace 10. As such, the orthopedic brace 210 has a frame 212. Elements of the frame 212, which correspond to like elements of the frame 12 of the orthopedic brace 10, are identified by the same reference number, but the reference number is additionally preceded by the numeral "2". Thus, for example, the frame 212 has upper and lower frame assemblies which are identified by the reference numbers 214 and 216, respectively.

The primary differences between the orthopedic brace 210 and the orthopedic brace 10 are the preferred configuration of the frame 212 as well as the preferred arrangement of the securing straps, and the preferred means by which the securing straps are attached or otherwise connected to the frame 212, as described hereafter. In particular, the frame 212 includes a lateral upper longitudinal support 222 having a distal end 236 which merges into the upper cuff 224 at the lateral end 252, rather than at an intermediate point 250. The frame 212 further includes a lower longitudinal support 228 having a distal end 240 which merges into the lower cuff 230 at the lateral end 256, rather than at an intermediate point 254. Thus, the lateral upper and lower longitudinal supports 222, 228 are oriented in alignment with the longitudinal axis of the leg 94 to which the orthopedic brace 210 is secured.

The construction of the lateral upper and lower longitudinal supports 222, 228 is preferably contoured to more closely conform each of the lateral upper and lower longitudinal supports 222, 228 to the contours of the leg 94 of a user to which the orthopedic brace 210 is to be secured. The construction of the upper and lower sidebars 260, 270 is similarly preferably contoured to more closely conform each of the sidebars 260, 270 to the contours of the leg 94 of the user. As such, the upper sidebar 260 and lateral upper longitudinal support 222 preferably converge at an angle toward one another as they approach the lateral and medial central joints 218, 220, respectively, in correspondence with the taper of the upper leg 96 as it approaches the knee 100. The lower sidebar 270 and lateral lower longitudinal support 228 similarly preferably converge at an angle toward one another as they approach the lateral and medial central joints 218, 220, respectively, in correspondence with the taper of the lower leg 98 as it approaches the knee 100.

The orthopedic brace 210 comprises a plurality of securing straps, namely, an upper proximal posterior strap 310, an upper proximal anterior strap 312, an upper distal posterior strap 314, a lower proximal posterior strap 316, a lower proximal anterior strap 318 and a lower distal posterior strap 320. The securing straps 310, 312, 314, 316, 318, 320 are each flexible, yet relatively non-stretchable, cloth straps which closely secure the orthopedic brace 210 to the leg 94.

The upper proximal posterior strap 310 is a partial circumferential strap which extends posteriorly around the upper leg 96 proximal to the knee 100 in a semi-circular path between the lateral and medial upper longitudinal supports 222, 226. The medial end of the upper proximal posterior strap 310 is threaded through an upper strap slot 322 which is formed through the medial upper longitudinal support 226. The lateral end of the upper proximal posterior strap 310 is threaded through an upper proximal posterior strap loop 324 which is fixably attached to the lateral upper longitudinal support 222 by a fastener, such as a rivet 86.

The upper proximal anterior strap 312 is a partial circumferential strap which extends anteriorly around the upper leg 96 proximal to the knee 100 in a semi-circular path between the lateral and medial upper longitudinal supports 222, 226. The medial end of the upper proximal anterior strap 312 is threaded through the upper strap slot 322 and the lateral end of the upper proximal anterior strap 312 is threaded through an upper proximal anterior strap loop 326 which is fixably attached to the lateral upper longitudinal support 222, preferably by the same fastener 86 fixably attaching the upper proximal posterior strap loop 324 to the lateral upper longitudinal support 222.

The upper distal posterior strap 314 is a partial circumferential strap which extends posteriorly around the upper leg 96 distal to the knee 100 in a semi-circular path between the lateral and medial ends 252, 266 of the upper cuff 224. The lateral end of the upper distal posterior strap 314 is threaded through an upper distal lateral strap loop 328 which is fixably attached to the lateral end 252 of the upper cuff 224 by a fastener 86. The medial end of the upper distal posterior strap 314 is threaded through an upper distal medial strap loop 330 which is fixably attached to the medial end 266 of the upper cuff 224 by a fastener 86.

The lower proximal posterior strap 316 is a partial circumferential strap which extends posteriorly around the lower leg 98 proximal to the knee 100 in a semi-circular path between the lateral and medial lower longitudinal supports 228, 232. The medial end of the lower proximal posterior strap 316 is threaded through a lower strap slot 332 formed through the medial lower longitudinal support 232. The lateral end of the lower proximal posterior strap 316 is threaded through a lower proximal posterior strap loop 334 which is fixably attached to the lateral lower longitudinal support 228 by a fastener 86.

The lower proximal anterior strap 318 is a partial circumferential strap which extends anteriorly around the lower leg 98 proximal to the knee 100 in a semi-circular path between the lateral and medial lower longitudinal supports 228, 232. The medial end of the lower proximal anterior strap 318 is threaded through the lower strap slot 332 and the lateral end of the lower proximal anterior strap 318 is threaded through a lower proximal anterior strap loop 336 which is fixably attached to the lateral lower longitudinal support 228, preferably by the same fastener 86 fixably attaching the lower proximal posterior strap loop 334 to the lateral lower longitudinal support 228.

The lower distal posterior strap 320 is a partial circumferential strap which extends posteriorly around the lower leg 98 distal to the knee 100 in a semi-circular path between the lateral and medial ends 256, 276 of the lower cuff 230. The lateral end of the lower distal posterior strap 320 is threaded through a lower distal lateral strap loop 338 which is fixably attached to the lateral end 256 of the lower cuff 230 by a fastener 86. The medial end of the lower distal posterior strap 320 is threaded through a lower distal medial strap loop 340 which is fixably attached to the medial end 276 of the lower cuff 230 by a fastener 86.

Each securing strap 310, 312, 314, 316, 318, 320 is fitted with first and second releasable fasteners 128, 130, preferably hook and loop fasteners, which enable a strap end having the first fastener 128 to be looped through one of the strap slots 322, 332 or one of the strap loops 324, 326, 328, 330, 334, 336, 338, 340, doubled back onto the second fastener 130 integral with the strap midsection, and fastened thereto. The user is able to adjust the strap length and strap tension by selection of the point on the second fastener 130 where the first fastener 128 is fastened. Accordingly, each of the securing straps 310, 312, 314, 316, 318, 320 may be tightened or loosened by shortening or lengthening the securing straps 310, 312, 314, 316, 318, 320, enabling the user to adjust the fit of the orthopedic brace 210 to the leg 94 and correspondingly to adjust the degree of support and stability the orthopedic brace 210 provides the knee 100.

As in the case of the orthopedic brace 10, it is understood that the specific construction of the offset hinges and the means of attaching designated offset hinges to corresponding adjacent members of the orthopedic brace 210 are recited above by way of example and are not intended to limit the present invention. Thus, it is within the scope of the present invention to alternately construct the offset hinges and to alternately effect attachment of the offset hinges and the corresponding adjacent members as taught above with respect to the orthopedic brace 10. It is further understood that the specific means of connecting the securing straps to corresponding members of the orthopedic brace 210 are recited above by way of example and are not intended to limit the present invention. Thus, it is within the scope of the present invention to employ alternate connection means as taught above with respect to the orthopedic brace 10. It is also within the scope of the present invention to omit the upper and/or lower cuffs 224, 230 from the frame 212 of the orthopedic brace 210 as taught above with respect to the orthopedic brace 10. It is still further within the scope of the present invention to cooperatively construct the sidebars 260, 270 and adjacent distal and proximal offset hinges 258, 262, 268, 272 in accordance with any of the alternatives taught above with respect to the orthopedic brace 10.

The specific configuration and characteristics of the above-described orthopedic brace 10 or 210 achieve a number of functional advantages when the orthopedic brace 10 or 210 is worn on the leg 94 of a user. In particular, the medial frame assembly of the orthopedic brace 10 or 210 has a substantially greater degree of flexibility (and conversely lower degree of rigidity) than the lateral frame assembly as the result of integrating at least one offset hinge (and in the present case four offset hinges 58, 62, 68, 72 or 258, 262, 268, 272) into the medial frame assembly. The asymmetrical flexibility character of the orthopedic brace 10 or 210 substantially enhances the fit of the orthopedic brace 10 or 210 on the leg 94 of the user without diminishing the support and stability functions of the orthopedic brace 10 or 210.

In accordance with a preferred embodiment, the frame 12 or 212, and more particularly the medial frame assembly, of the orthopedic brace 10 or 210 is sized and configured relative to the leg 94 of the user so that the medial frame assembly does not exert any substantial linear biasing forces on the leg 94 including the knee 100 in the lateral direction when the orthopedic brace 10 or 210 is placed on the leg 94, but before the orthopedic brace 10 or 210 is closely secured to the leg 94 by connecting and tightening the securing straps. As such, the frame 12 or 212, and more particularly the medial frame assembly, is deemed force neutral with respect to the leg 94 when the orthopedic brace 10 or 210 is placed on the leg 94 in an unsecured state. When the securing straps are connected and tightened with sufficient tension to secure the orthopedic brace 10 or 210 to the leg 94, the relatively flexible medial frame assembly is deformed by bending, and in some cases twisting, to bring the frame 12 into close-fitting alignment and conformance with the medial longitudinal profile of the leg 94, while maintaining the force neutrality of the medial frame assembly with respect to the leg 94.

In accordance with an alternate embodiment, the frame 12 or 212, and more particularly the medial frame assembly, of the orthopedic brace 10 or 210 is sized and configured relative to the leg 94 of the user so that the medial frame assembly exerts a substantial linear biasing forces on the leg 94 including the knee 100 in the lateral direction when the orthopedic brace 10 or 210 is placed on the leg 94 even before the orthopedic brace 10 or 210 is closely secured to the leg 94 by connecting and tightening the securing straps. As such, the frame 12 or 212, and more particularly the medial frame assembly, applies a biasing force on the leg 94 when the orthopedic brace 10 or 210 is placed on the leg 94 in an unsecured state. When the securing straps are connected and tightened with sufficient tension to secure the orthopedic brace 10 or 210 to the leg 94, the relatively flexible medial frame assembly is deformed by bending, and in some cases twisting, to bring the frame 12 into close-fitting alignment and conformance with the medial longitudinal profile of the leg 94, while maintaining the biasing force of the medial frame assembly on the leg 94.

The precise fit of the orthopedic brace 10 or 210 beneficially enhances the suspension of the orthopedic brace 10 or 210 on the leg 94. Suspension is the ability of the orthopedic brace 10 or 210 to retain its proper placement on the leg 94 during routine user activity. The close-fitting orthopedic brace 10 or 210 resists undesirable downward and/or rotational migration of the orthopedic brace 10 or 210 on the leg 94 during routine user activity. Enhanced suspension correspondingly enhances the functional performance of the orthopedic brace 10 or 210 and the comfort of the user. The precise fit of the orthopedic brace 10 or 210 also enhances the degree of intimate contact between the orthopedic brace 10 or 210 and the leg 94. Enhanced intimate contact correspondingly enhances the functional performance of the orthopedic brace 10 or 210.

The asymmetrical flexibility character of the orthopedic brace 10 or 210 advantageously enables the medial central joint 20 or 220 to "float" relative to the lateral central joint 18 or 218. In particular, the upper and lower proximal offset hinges 62, 72 or 262, 272 enable displacement of the upper and lower central connectors 64, 74 or 264, 274, which can produce canting of the medial central joint 20 or 220 relative to the knee 100. The lower end of the canted medial central joint 20 or 220 is angled in a medial or lateral direction away from vertical and the upper end of the canted medial central joint 20 or 220 is angled in the opposite direction from vertical. In the case where the lateral and medial central joints 18, 20 or 218, 220 are rotational hinges, canting of the medial central joint 20, 220 results in the medial central joint 20, 220 having an axis of rotation, which is out of alignment, i.e., no longer correspondent or parallel, with the axis of rotation of the lateral central joint 18, 218.

The higher degree of flexibility of the asymmetrically flexible orthopedic brace 10 or 210 is preferably assigned to the medial side rather than the lateral side of the orthopedic brace 10 or 210 to realize certain beneficial effects. In particular, when the orthopedic brace 10 or 210 is used to support and/or stabilize the medial collateral ligament (MCL), rigid support to the lateral side of the knee 100 is more beneficial than to the medial side of the knee 100. When a lateral load is applied to the orthopedic brace 10 or 210, the brace 10 or 210 displays a sling effect wherein the rigid lateral frame assembly bears the bulk of the load to substantially inhibit undesirable lateral displacement of the knee 100, despite the presence of the relatively flexible medial frame assembly on the opposite side of the orthopedic brace 10 or 210. Accordingly, the flexible medial frame assembly advantageously enhances the fit of the orthopedic brace 10 or 210 on the leg 94 without negating the beneficial effect of the relatively rigid lateral frame assembly on the MCL.

When the present orthopedic braces 10 or 210 are worn on both the right and left legs of a user, securing the orthopedic braces 10 or 210 to each leg advantageously draws the medial frame assemblies of each orthopedic brace 10 or 210 laterally away from one another to provide greater clearance between the two orthopedic braces 10 or 210 during routine user activity and to avoid undesirable contact between the two orthopedic braces 10 or 210.

When the orthopedic brace 10 or 210 is an osteoarthritic brace, as described in U.S. Pat. Nos. 5,807,294 and 5,458,565, for example, it is often desirable for the lateral frame assembly to exert a linear biasing force on the knee 100 in a medial direction. The flexible medial frame assembly on the opposite side of the orthopedic brace advantageously yields somewhat to the medially directed force to prevent the lateral frame assembly from uncomfortably pinching the knee 100 against the medial frame assembly, but not negating the beneficial effect of the medially directed force applied to the knee 100 by the relatively rigid lateral frame assembly.

The higher degree of flexibility of the asymmetrically flexible orthopedic brace of the present invention is alternatively beneficially assigned to the lateral side rather than the medial side of the orthopedic brace under certain conditions simply by reversing the above-recited construction of the medial and lateral frame assemblies. For example, in some instances when the orthopedic brace 10 or 210 is an osteoarthritic brace, it may be desirable for the medial frame assembly to exert a linear biasing force on the knee 100 in a lateral direction. The flexible lateral frame assembly on the opposite side of the orthopedic brace advantageously yields somewhat to the medially directed force to prevent the medial frame assembly from uncomfortably pinching the knee 100 against the lateral frame assembly, but not negating the beneficial effect of the laterally directed force applied to the knee 100 by the relatively rigid medial frame assembly.

While the forgoing preferred embodiments of the invention have been described and shown, it is understood that alternatives and modifications, such as those suggested and others, may be made thereto and fall within the scope of the invention.

GLOSSARY OF DRAWING TERMS

10 orthopedic brace
12 frame
14 upper frame assembly
16 lower frame assembly
18 lateral central joint
20 medial central joint
22 lateral upper longitudinal support (14)
24 upper cuff (14)
26 medial upper longitudinal support (14)
28 lateral lower longitudinal support (16)
30 lower cuff (16)
32 medial lower longitudinal support (16)
lateral frame assembly (22, 18, 28)
medial frame assembly (26, 20, 32)
34 proximal end (22)
36 distal end (22)
38 proximal end (28)
40 distal end (28)
42 proximal end (26)
44 distal end (26) (60)
46 proximal end (32)
48 distal end (32)
50 intermediate point (24)
52 lateral end (24)
54 intermediate point (30)
56 lateral end (30)
58 upper distal offset hinge (26)
60 upper sidebar (26)
62 upper proximal offset hinge (26)
64 upper central connector (26)
66 medial end (24)
68 lower distal offset hinge (32)
70 lower sidebar (32)
72 lower proximal offset hinge (32)
74 lower central connector (32)
76 medial end (30)
78 deformation section (58)
80 distal attachment section (58)
82 proximal attachment section (58)
84 - -
86 rivets
88 lateral condyle cup
90 medial condyle cup
92 strap anchor
94 left leg
96 upper leg
98 lower leg
100 knee
102 lateral condyle pad
104 medial condyle pad
106 upper frame padding 108 lower frame padding
110 upper proximal strap
112 upper distal strap
114 lower proximal strap
116 lower distal strap
118 upper strap slots (60)
120 releasable internal strap retainer
122 releasable external strap retainer
124 fixed strap retainer
126 lower strap slots (70)
128 first fastener
130 second fastener
210 orthopedic brace
212 frame
214 upper frame assembly
216 lower frame assembly
218 lateral central joint
220 medial central joint
222 lateral upper longitudinal support (214)
224 upper cuff (214)
226 medial upper longitudinal support (214)
228 lateral lower longitudinal support (216)
230 lower cuff (216)
232 medial lower longitudinal support (216)
lateral frame assembly (222, 218, 228)
medial frame assembly (226, 220, 232)
234 proximal end (222)
236 distal end (222)
238 proximal end (228)
240 distal end (228)
242 proximal end (226)
244 distal end (226) (260)
246 proximal end (232)
248 distal end (232)
250 intermediate point (224)
252 lateral end (224)
254 intermediate point (230)
256 lateral end (230)
258 upper distal offset hinge (226)
260 upper sidebar (226)
262 upper proximal offset hinge (226)
264 upper central connector (226)
266 medial end (224)
268 lower distal offset hinge (232)
270 lower sidebar (232)
272 lower proximal offset hinge (232)
274 lower central connector (232)
276 medial end (230)
278 deformation section (258)
280 distal attachment section (258)
282 proximal attachment section (258)
310 upper proximal posterior strap
312 upper proximal anterior strap
314 upper distal posterior strap
316 lower proximal posterior strap
318 lower proximal anterior strap
320 lower distal posterior strap
322 upper strap slot (226)
324 upper proximal posterior strap loop
326 upper proximal anterior strap loop
328 upper distal lateral strap loop
330 upper distal medial strap loop
332 lower strap slot (232)
334 lower proximal posterior strap loop
336 lower proximal anterior strap loop
338 lower distal lateral strap loop
340 lower distal medial strap loop

We claim:

1. A frame for an orthopedic brace comprising:
a frame assembly including a first longitudinal support and a second longitudinal support rotatably connected by a rotational hinge, said first longitudinal support including a first frame member, a second frame member, and a first offset hinge connecting said first and second frame members, wherein said first offset hinge has a greater degree of flexibility than said first and second frame members;
an opposing frame assembly including a first opposing longitudinal support having a rigid unitary structure and a second opposing longitudinal support rotatably connected by an opposing rotational hinge, wherein said first longitudinal support has a greater degree of flexibility than said first opposing longitudinal support;
a frame assembly member connecting said first longitudinal support and said first opposing longitudinal support, wherein said frame assembly member is rigidly connected to said first opposing longitudinal support; and
a second offset hinge included in said first longitudinal support connecting said second frame member and said frame assembly member, said second offset hinge having a greater degree of flexibility than said second frame member and said frame assembly member to flexibly connect said frame assembly member to said first longitudinal support.

2. The frame of claim 1, wherein said first longitudinal support is an upper longitudinal support, said second longitudinal support is a lower longitudinal support, said first frame member is an upper first frame member, said second frame member is an upper second frame member, said frame assembly member is an upper frame assembly member, said first offset hinge is an upper first offset hinge and said second offset hinge is an upper second offset hinge, further wherein said lower longitudinal support includes a lower first frame member, a lower second frame member, and a lower first offset hinge connecting said lower first and second frame members and having a greater degree of flexibility than said lower first and second frame members.

3. The frame of claim 2, wherein said frame assembly further includes a lower frame assembly member connecting said lower longitudinal support and said lower opposing longitudinal support, and wherein said lower longitudinal support further includes a lower second offset hinge connecting said lower second frame member and said lower frame assembly member, said lower second offset hinge having a greater degree of flexibility than said lower first frame member and said lower frame assembly member.

4. The frame of claim 1, wherein said frame is for a knee brace.

5. The frame of claim 1, wherein said frame assembly is a medial frame assembly and said opposing frame assembly is a lateral frame assembly.

6. The frame of claim 1, wherein said frame assembly is a lateral frame assembly and said opposing frame assembly is a medial frame assembly.

7. The frame of claim 1, wherein said first frame member is a central connector engaging said rotational hinge and said second frame member is a sidebar, wherein said central connector is constructed from a metal, said sidebar is constructed from a metal or a plastic and said first offset hinge is constructed from said plastic of said sidebar or from a different plastic.

8. The frame of claim 1, wherein said first frame member is a central connector engaging said rotational hinge and said second frame member is a sidebar, wherein said central connector is constructed from a metal, said first offset hinge is constructed from a plastic and said first offset hinge is attached to said central connector by overmolding.

9. The frame of claim 1, wherein said frame assembly member is a cuff and said second frame member is a sidebar, wherein said cuff is constructed from a metal, said sidebar is constructed from a metal or a plastic and said second offset hinge is constructed from said plastic of said sidebar or from a different plastic.

10. The frame of claim 1, wherein said frame assembly member is a cuff and said second frame member is a sidebar, wherein said cuff is constructed from a metal, said second offset hinge is constructed from a plastic and said second offset hinge is attached to said cuff by overmolding or by at least one fastener.

11. The frame of claim 1, wherein said greater degree of flexibility is in a mediolateral direction.

12. The frame of claim 1, wherein said first and second offset hinges are living hinges.

13. A frame for an orthopedic brace comprising:
- a medial frame assembly including a medial upper longitudinal support and a medial lower longitudinal support connected by a medial central joint, wherein said medial upper longitudinal support includes a first upper frame member and a second upper frame member connected by an upper offset hinge, said first and second upper frame members being less flexible than said upper offset hinge, and further wherein said medial lower longitudinal support includes a first lower frame member and a second frame lower member connected by a lower offset hinge, said first and second lower frame members being less flexible than said lower offset hinge;
- a lateral frame assembly including a lateral upper longitudinal support having a rigid unitary structure and a lateral lower longitudinal support having a rigid unitary structure connected by a lateral central joint, wherein said lateral frame assembly is more rigid than said medial frame assembly;
- an upper cuff connecting said medial upper longitudinal support and said lateral upper longitudinal support, wherein said lateral upper longitudinal support is rigidly connected to said upper cuff by rigid fixed attachment thereto and said medial upper longitudinal support is flexibly connected to said upper cuff; and
- a lower cuff connecting said medial lower longitudinal support and said lateral lower longitudinal support, wherein said lateral lower longitudinal support is rigidly connected to said lower cuff by rigid fixed attachment thereto and said medial lower longitudinal support is flexibly connected to said upper cuff.

14. The frame of claim 13 wherein said upper offset hinge is a first upper offset hinge, said frame further comprising a second upper offset hinge flexibly connecting said upper cuff and said second upper frame member.

15. The frame of claim 13 wherein said lower offset hinge is a first lower offset hinge, said frame further comprising a second lower offset hinge flexibly connecting said lower cuff and said second lower frame member.

16. The frame of claim 13, wherein said upper and lower offset hinges are living hinges.

17. A frame for an orthopedic brace comprising:
- a frame assembly including an upper longitudinal support and a lower longitudinal support rotatably connected by a rotational hinge essentially rigid in a mediolateral direction, said upper longitudinal support including a first upper frame member, a second upper frame member, a first upper offset hinge, and a second upper offset hinge, wherein said first upper offset hinge connects said first and second upper frame members and has a greater degree of flexibility than said first and second upper frame members in said mediolateral direction, and said lower longitudinal support including a first lower frame member, a second lower frame member, a first lower offset hinge, and a second lower offset hinge, wherein said first lower offset hinge connects said first and second lower frame members and has a greater degree of flexibility than said first and second lower frame members in said mediolateral direction;
- an opposing frame assembly including an upper opposing longitudinal support and a lower opposing longitudinal support rotatably connected by an opposing rotational hinge, wherein said upper longitudinal support has a greater degree of flexibility than said upper opposing longitudinal support and/or said lower longitudinal support has a greater degree of flexibility than said lower opposing longitudinal support;
- an upper frame assembly member connecting said upper longitudinal support and said upper opposing longitudinal support, wherein said second upper offset hinge connects said second upper frame member and said upper frame assembly member and has a greater degree of flexibility than said second upper frame member and said upper frame assembly member in said mediolateral direction; and
- a lower frame assembly member connecting said lower longitudinal support and said lower opposing longitudinal support, wherein said second lower offset hinge connects said second lower frame member and said lower frame assembly member and has a greater degree of flexibility than said second lower frame member and said lower frame assembly member in said mediolateral direction.

18. The frame of claim 17, wherein said frame assembly is a medial frame assembly and said opposing frame assembly is a lateral frame assembly.

19. The frame of claim 17, wherein said frame assembly is a lateral frame assembly and said opposing frame assembly is a medial frame assembly.

20. The frame of claim 17, wherein said first upper or lower frame member is a central connector engaging said rotational hinge and said second upper or lower frame member is a sidebar, wherein said central connector is constructed from a metal, said sidebar is constructed from a metal or a plastic and said first upper or lower offset hinge is constructed from said plastic of said sidebar or from a different plastic.

21. The frame of claim 17, wherein said first upper or lower frame member is a central connector engaging said rotational hinge and said second upper or lower frame member is a sidebar, wherein said central connector is constructed from a metal, said first upper or lower offset hinge is constructed from a plastic and said first upper or lower offset hinge is attached to said central connector by overmolding.

22. The frame of claim 17, wherein said upper or lower frame assembly member is a cuff and said second upper or lower frame member is a sidebar, wherein said cuff is constructed from a metal, said sidebar is constructed from a metal or a plastic and said second upper or lower offset hinge is constructed from said plastic of said sidebar or from a different plastic.

23. The frame of claim 17, wherein said upper or lower frame assembly member is a cuff and said second upper or lower frame member is a sidebar, wherein said cuff is constructed from a metal, said second upper or lower offset hinge is constructed from a plastic and said second upper or lower offset hinge is attached to said cuff by overmolding or at least one fastener.

24. The frame of claim 17, wherein said first and second upper offset hinges and said first and second lower offset hinges are living hinges.

25. A method for precisely fitting a knee brace with a leg of a user comprising:

providing a knee brace having a frame assembly, an opposing frame assembly, an upper cuff and a lower cuff, said frame assembly including an upper longitudinal support and a lower longitudinal support rotatably connected by a central joint, wherein said upper longitudinal support includes a first upper frame member and a second upper frame member flexibly connected by a first upper offset hinge, being less flexible than said first and second upper frame members, a first lower frame member and a second lower frame member flexibly connected by a first lower offset hinge being less flexible than said first and second lower frame members and said opposing frame assembly including an opposing upper longitudinal support and an opposing lower longitudinal support rotatably connected by an opposing lateral central joint, said opposing upper longitudinal support having a rigid unitary structure and rigidly connected to said upper cuff by rigid fixed attachment thereto and said opposing lower longitudinal support having a rigid unitary structure and rigidly connected to said lower cuff by rigid fixed attachment thereto, wherein said upper longitudinal support further includes a second upper offset hinge flexibly connecting said second upper frame member and said upper cuff, said upper second offset hinge having a greater decree of flexibility than said second upper frame member and said upper cuff, and said lower longitudinal support further includes a second lower offset hinge flexibly connecting said second lower frame member and said lower cuff, said second lower offset hinge having a greater degree of flexibility than said second lower frame member and said lower cuff, placing said knee brace on a leg having an upper leg, a lower leg and a knee, such that said upper longitudinal support and said opposing upper longitudinal support are adjacent said upper leg on essentially opposite sides of said upper leg, said lower longitudinal support and said opposing lower longitudinal support are adjacent said lower leg and on essentially opposite sides of said lower leg, and said medial central joint and opposing central joint are adjacent said knee and on opposite sides of said knee; and connecting at least one strap to said upper longitudinal support and said opposing upper longitudinal support and/or to said lower longitudinal support and said opposing lower longitudinal support with sufficient tension to bendably deform said upper longitudinal support and/or said lower longitudinal support at said first and second upper offset hinges and/or at said first and second lower offset hinges into close fitting conformance with said upper leg and/or said lower leg.

26. The method of claim 25, wherein said frame assembly is force neutral with respect to said leg when said knee brace is placed on said leg and before connecting said at least one strap.

27. The method of claim 25, wherein said first and second upper offset hinges and said first and second lower offset hinges are living hinges.

* * * * *

UNITED STATES PATENT AND TRADEMARK OFFICE
CERTIFICATE OF CORRECTION

PATENT NO.         : 7,479,122 B2                                                 Page 1 of 1
APPLICATION NO.    : 11/040814
DATED              : January 20, 2009
INVENTOR(S)        : Dylann D. Ceriani et al.

It is certified that error appears in the above-identified patent and that said Letters Patent is hereby corrected as shown below:

Claim 25 at column 23, line 16 and at column 23, line 19:
delete "less" and insert --more--.

Signed and Sealed this

Sixteenth Day of June, 2009

JOHN DOLL
*Acting Director of the United States Patent and Trademark Office*